United States Patent
Martinic et al.

(10) Patent No.: US 10,458,991 B2
(45) Date of Patent: Oct. 29, 2019

(54) SELECTIVE NEAR-INFRARED OPTICAL IMAGING OF NECROTIC CELLS AND SIMULTANEOUS CELL FIXING AND COUNTER STAINING WITH METALLACROWN COMPLEXES

(71) Applicants: THE REGENTS OF THE UNIVERSITY OF MICHIGAN, Ann Arbor, MI (US); CENTRE NATIONAL DE LA RECHERCHE SCIENTIFIQUE, Paris (FR)

(72) Inventors: Ivana Martinic, Orléans (FR); Tu Ngoc Nguyen, Ann Arbor, MI (US); Svetlana V. Eliseeva, Orléans (FR); Vincent L. Pecoraro, Ann Arbor, MI (US); Stéphane Petoud, Orléans (FR)

(73) Assignees: The Regents of the University of Michigan, Ann Arbor, MI (US); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 15/752,870

(22) PCT Filed: Aug. 12, 2016

(86) PCT No.: PCT/EP2016/069296
§ 371 (c)(1),
(2) Date: Feb. 14, 2018

(87) PCT Pub. No.: WO2017/029242
PCT Pub. Date: Feb. 23, 2017

(65) Prior Publication Data
US 2018/0238897 A1 Aug. 23, 2018

Related U.S. Application Data

(60) Provisional application No. 62/205,053, filed on Aug. 14, 2015.

(51) Int. Cl.
*G01N 33/00* (2006.01)
*G01N 33/58* (2006.01)
*C07F 3/06* (2006.01)
*G01N 21/64* (2006.01)
*G01N 21/33* (2006.01)
*G01N 1/30* (2006.01)
*C07F 5/00* (2006.01)

(52) U.S. Cl.
CPC ............ *G01N 33/583* (2013.01); *C07F 3/06* (2013.01); *C07F 5/003* (2013.01); *G01N 1/30* (2013.01); *G01N 21/33* (2013.01); *G01N 21/6458* (2013.01); *G01N 2001/302* (2013.01); *G01N 2001/305* (2013.01); *G01N 2021/6439* (2013.01)

(58) Field of Classification Search
CPC ......... C07F 5/003; C07F 3/06; G01N 33/583; C12N 5/00
See application file for complete search history.

(56) References Cited

U.S. PATENT DOCUMENTS

2015/0297602 A1  10/2015  Lambert et al.

FOREIGN PATENT DOCUMENTS

WO  WO 2015/035196 A1  3/2015
WO  WO 2016/166380 A1  10/2016

OTHER PUBLICATIONS

Dasari, M. et al. 2010 "Hoechst-IR: In imaging agent that detects necrotic tissue in vivo by binding extracellular DNA" *Org Let* 12(15): 3300-3303.

Trivedi, E.R. et al. 2014 "Highly emitting near-infrared lanthanide 'encapsulated sandwich' metallacrown complexes with excitation shifted toward lower energy" *J Am Chem Soc* 136: 1526-1534.

*Primary Examiner* — Ruth A Davis
(74) *Attorney, Agent, or Firm* — Knobbe, Martens Olson & Bear LLP

(57) ABSTRACT

In an example of a method for simultaneously fixing and staining cells, the cells are initially incubated in a solution including a $Ln(III)Zn_{16}(HA\ ligand)_{16}$ metallacrown complex, wherein the HA ligand is a hydroximate ligand. The incubating cells are exposed to ultraviolet (UV) light. The cells are allowed to continue to incubate in the solution after UV light exposure.

12 Claims, 19 Drawing Sheets

A.

B.

C.

SELECTIVE NEAR-INFRARED OPTICAL IMAGING OF NECROTIC CELLS AND SIMULTANEOUS CELL FIXING AND COUNTER STAINING WITH METALLACROWN COMPLEXES

STATEMENT REGARDING FEDERALLY SPONSORED R&D

This invention was made with government support under CHE1361779, awarded by the U.S. National Science Foundation. The government has certain rights in the invention.

BACKGROUND

Optical devices, bioanalytical assays, and biological imaging probes often utilize components that exhibit optical properties, such as organic fluorophores and semi-conductor nanoparticles. Some desired optical properties include long luminescence lifetimes, large effective energy differences between excitation and emission bands, and sharp emission bands throughout the visible and near-infrared (NIR) spectral ranges. NIR optical imaging has clinical potential to significantly improve diagnosis of various human diseases in real time imaging experiments. Currently used nucleic acid-binding NIR dyes (e.g., organic fluorophores) are not fully reliable for optical imaging, in part because of low quantum yield, broad bandwith, high energy excitation wavelengths, small Stokes shift, poor water solubility, and low photostability (i.e., prone to photobleaching). These characteristics of nucleic acid-binding NIR dyes can limit detection sensitivity and deleteriously affect image resolution. While quantum dots have better resistance to photobleaching and higher quantum yields than nucleic acid-binding NIR dyes, these imaging agents may suffer from blinking (i.e., random fluctuations in light emission) and may be toxic for in vivo applications.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 20. (C) and (D) are graphs illustrating the corrected and normalized excitation ($\lambda_{em}$=980 nm) and emission spectra ($\lambda_{ex}$=370 nm), respectively, of Yb$^{3+}$[Zn(II)MC$_{pyzHA}$] complexes in cell supernatant and in HeLa cells treated with N-aceytal cysteine, both with and without UV exposure;

FIGS. 20. (E) and (F) are graphs illustrating the corrected and normalized excitation ($\lambda_{em}$=1064 nm) and emission spectra ($\lambda_{ex}$=370 nm), respectively, of Nd$^{3+}$[Zn(II)MC$_{pyzHA}$] complexes in OPTI-MEM® media and in HeLa cells, both with and without UV exposure;

Figure 1:
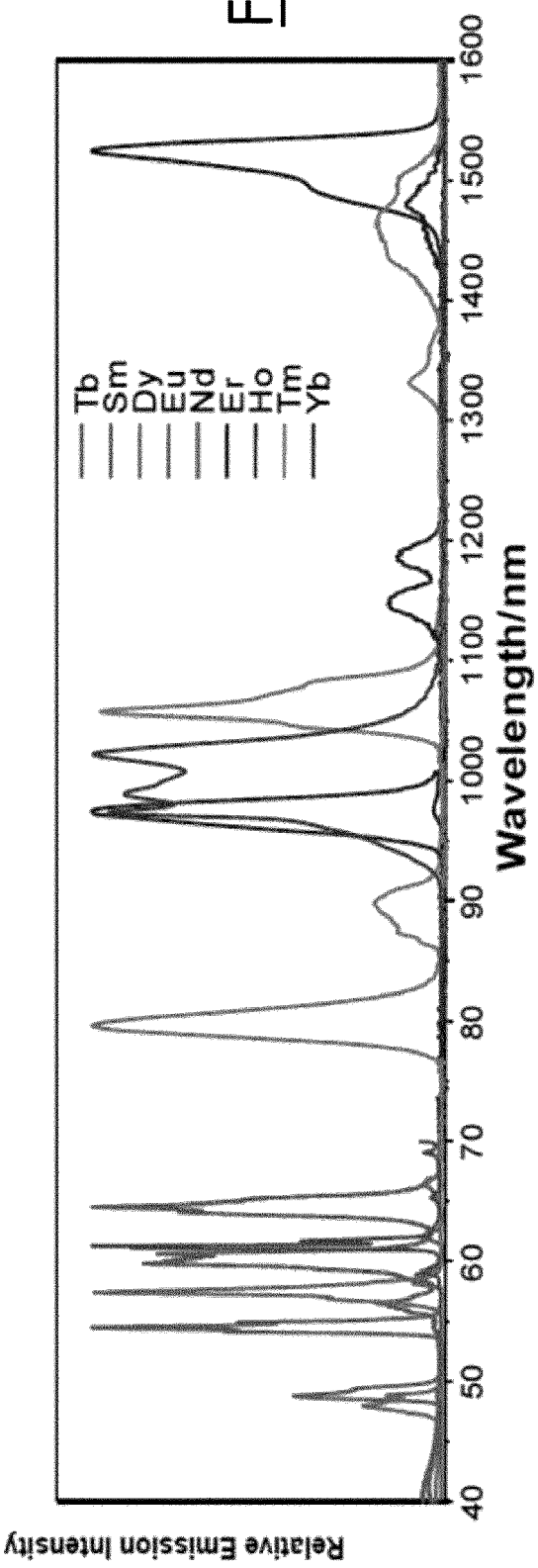
FIG. 1 is a graph illustrating the normalized emission spectra of lanthanides.

TABLE 1 illustrates the photophysical properties of $Yb^{3+}[Zn(II)MC_{pyzHA}]$ and $Nd^{3+}[Zn(II)MC_{pyzHA}]$ MCs in solid state and in aqueous solutions (200 μM) at room temperature.[a]

| | $\tau(\mu s)$[b] | | | | $Q(\%)$[d] | | |
|---|---|---|---|---|---|---|---|
| Metallacrown | Solid | $H_2O$ | $D_2O$ | $q^c$ | Solid | $H_2O$ | $D_2O$ |
| $Yb^{3+}[Zn(II)MC_{pyzHA}]$ | 45.6(3) | 5.57(1) | 81.3(1) | 0 | 0.659(4) | $1.12(7) \cdot 10^{-2}$ | 0.257(3) |
| $Nd^{3+}[Zn(II)MC_{pyzHA}]$ | 1.71(1) | 0.214(4) | 1.29(1) | 0.1 | 0.444(9) | $7.7(1) \cdot 10^{-3}$ | $6.17(9) \cdot 10^{-2}$ |

[a] 2σ values are given between parentheses. Experimental errors: τ, ±2%, Q, ±10%.
[b] Under excitation at 355 nm.
[c] The number of coordinated water molecules (q) has been calculated using the equations:

$$q_{Yb} = \frac{1}{\tau_{H2O}} - \frac{1}{\tau_{D2O}} - 0.2 \text{ (in } \mu s) \text{ and } q_{Nd} = 130 \times \left(\frac{1}{\tau_{H2O}} - \frac{1}{\tau_{D2O}}\right) - 0.4;$$

[274, 275] estimated error ±0.2.
[d] Under excitiation at 370 nm.

DESCRIPTION

The present invention relates to a method for simultaneously fixing and staining cells, preferably in vitro, the method comprising:
initially incubating the cells in a solution including a Ln(III) $Zn_{16}$(HA ligand)$_{16}$ metallacrown complex, wherein the HA ligand is a hydroximate ligand;

exposing the incubating cells to ultraviolet (UV) light; and continuing to incubate the cells in the solution after UV light exposure.

The present invention involves the use of a $Ln(III)Zn_{16}$(HA ligand)$_{16}$ metallacrown complex, wherein the HA ligand is a hydroximate ligand.

The metallacrown complexes used according to the invention may also be represented by the general formula $Ln^{3+}[Zn(II)MC_{HA}]$, wherein the HA ligand is a hydroximate ligand.

The preferred HA ligand will be described in detail hereafter. Preferably, the HA ligand is pyrazinehydroximate.

According to an embodiment, the metallacrown complex according to the invention may be represented by the following formula: $Ln^{3+}[Zn(II)MC_{pyzHA}]$.

According to an embodiment, the above-mentioned solution includes the $Ln(III)Zn_{16}$(HA ligand)$_{16}$ metallacrown complex in a medium; and a concentration of the $Ln(III)Zn_{16}$(HA ligand)$_{16}$ metallacrown complex in the solution ranges from about 90 μM to about 400 μM.

According to an embodiment, the method according to the invention further comprises culturing the cells prior to incubating the cells in the solution.

Preferably, the method according to the invention comprises the following steps:
  initially incubating the cells is accomplished for a time (T1) ranging from about 10 minutes to about 3 hours;
  exposing the incubating cells to UV light is accomplished for a time (T2) ranging from about 5 minutes to about 10 minutes; and
  continuing to incubate the cells is accomplished for a time (T3) ranging from about 1 hour to about 2 hours.

Preferably, the method according to the invention further comprises exposing the incubating cells to additional UV light for a time (T4) ranging from about 1 minute to about 5 minutes.

According to a preferred embodiment, the HA ligand of the $Ln(III)Zn_{16}$(HA ligand)$_{16}$ metallacrown complex is selected from the group consisting of pyrazinehydroximate, quinoxalinehydroximate, quinaldinehydroximate, and combinations thereof.

Preferably, the $Ln(III)Zn_{16}$(HA ligand)$_{16}$ metallacrown complex is one of:
  [$Ln(III)Zn_{16}$(pyrazinehydroximate)$_{16}$(pyridine)$_8$] counter ion;
  [$Ln(III)Zn_{16}$(quinoxalinehydroximate)$_{16}$(pyridine)$_8$] counter ion; or
  [$Ln(III)Zn_{16}$(quinaldinehydroximate)$_{16}$(pyridine)$_8$] counter ion;
  the Ln(III) is selected from the group consisting of $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$; and
  the counter ion is selected from the group consisting of a triflate, a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a phosphate, and a sulfonate.

According to an embodiment, the $Ln(III)Zn_{16}$(HA ligand)$_{16}$ metallacrown complex includes a mixture of metallacrown complexes; each species in the metallacrown mixture is [$Ln(III)Zn_{16}$(pyrazinehydroximate)$_x$(quinoxalinehydroximate)$_y$(pyridine)$_8$] counter ion, wherein x+y=16, wherein preferably x ranges from 8 to 13 and y ranges from 3 to 8;
  the Ln(III) is selected from the group consisting of $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$; and
  the counter ion is selected from the group consisting of a triflate, a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a phosphate, and a sulfonate.

According to an embodiment, the above-mentioned medium is a serum-supplemented medium.

Preferably, the UV light is UV-A light.

According to a preferred embodiment, in the method according to the invention, UV light exposure induces death of at least some of the cells; and after continuing to incubate the cells, the $Ln(III)Zn_{16}$(HA ligand)$_{16}$ metallacrown complex is located in nuclei and cytoplasm of least some dead cells.

The present invention also relates to an optical imaging method, preferably in vitro, comprising:
  forming simultaneously fixed and stained cells by:
    initially incubating cells in a solution including a $Ln(III)Zn_{16}$(HA ligand)$_{16}$ metallacrown complex, wherein the HA ligand is a hydroximate ligand;
    exposing the incubating cells to ultraviolet (UV) light; and
    continuing to incubate the cells in the solution after UV light exposure; and
  exposing the simultaneously fixed and stained cells to an optical imaging technique selected from the group consisting of epifluorescence microscopy, confocal microscopy, and combinations thereof.

According to an embodiment, the optical imaging method as mentioned above further comprising any of:
  tuning an excitation response of the simultaneously fixed and stained cells by changing the Ln(III) of the $Ln(III)Zn_{16}$(HA ligand)$_{16}$ metallacrown complex; or
  tuning an emission response of the simultaneously fixed and stained cells by changing the hydroximate ligand of the $Ln(III)Zn_{16}$(HA ligand)$_{16}$ metallacrown complex.

The present invention also relates to a method for selective labelling of necrotic cells, preferably in vitro, the method comprising incubating the cells in a solution including a $Ln(III)Zn_{16}$(HA ligand)$_{16}$ metallacrown complex, wherein the HA ligand is a hydroximate ligand.

According to an embodiment, the $Ln(III)Zn_{16}$(HA ligand)$_{16}$ metallacrown complex is as defined above.

DETAILED DESCRIPTION

In the example methods disclosed herein, lanthanide-based metallacrown complexes are used as probes for necrotic cells. In particular, the lanthanide-based metallacrown complexes operate as NIR and/or visible stains for the nucleus and the cytoplasm of the necrotic cells. In addition, the present inventors have found that a combination of short exposure to ultraviolet (UV) light and a high concentration of the lanthanide-based metallacrown complex brings about a photochemical effect, which is similar to cell fixation that may be obtained using formaldehyde or methanol. Fixing the dead cells in the manner disclosed herein preserves the morphology of the dead cells, and thus the fixed cells do not dissolve or decay.

As such, in the examples disclosed herein, the cells are simultaneously stained and fixed. "Simultaneously stained and fixed" means that the cells are exposed to counter staining and undergo fixation during the same procedure, and the acts of staining and fixing may occur at exactly the same time. Examples of the staining and mixing method will be discussed in more detail below.

As mentioned above, lanthanide-based metallacrown complexes are utilized as optical imaging agents/probes and cell fixation agents. Lanthanide(III) metal ions (Ln(III) or $Ln^{3+}$) contain 4f orbitals and exhibit unique luminescent characteristics. However, most f-f transitions of $Ln^{3+}$ ions are forbidden by quantum mechanics rules inducing low absorption coefficients, resulting in inefficient direct excitation. As such, use of the lanthanide signal in optical imaging is uncommon. In the examples disclosed herein, the structure of the lanthanide-based metallacrown complex may be controlled during its formation to provide optimized sensitization of the lanthanide cation, as well as protection against non-radiative deactivations.

The lanthanide-based metallacrown complexes disclosed herein are three-component supramolecular assemblies with transition metals, tetra-dentate ligands that are capable of transferring energy to a central ion and/or producing a ligand-based charge transfer state when incorporated into the metallacrown complex, and lanthanide ions ($Ln^{3+}$). The tetra-dentate ligands cyclize to form a repeating [—M—N—O—]$_x$ sub-unit, where M is the transition metal ion. Similar to crown ethers, metallacrowns can be synthesized with a range of sizes, and the inward facing oxime oxygen atoms are capable of binding to a central metal ion.

As mentioned above, the structure of the lanthanide-based metallacrown complex may be controlled to achieve a desired response. For example, by changing the ligand of the lanthanide-based metallacrown complex, the excitation response of the metallacrown complex may be altered. For another example, by changing the lanthanide metal, the emission response of the metallacrown complex may be altered. Characteristic NIR emission (i.e., NIR luminescence properties) of the lanthanide metal ions in the lanthanide-based metallacrown complexes disclosed herein may be observed under excitation wavelengths ranging from the UV to the visible range.

In the examples disclosed herein, the lanthanide-based metallacrown complexes may be referred to as Ln(III)TM$_{16}$(HA ligand)$_{16}$ metallacrown complexes, where Ln(III) is the lanthanide metal ion, TM is the transition metal ion, and HA ligand is the hydroximate ligand. The chemical formula of the metallacrown complex includes at least 1 lanthanide metal ion, 16 transition metal ions and 16 HA ligands. The 16 transition metal ions and 16 HA ligands are distributed among two capping crowns (i.e., [12-MC-4]$_2$) and an encapsulating crown (i.e., [24-MC-8]) which together form the entire metallacrown complex. Using metallacrown nomenclature, the lanthanide-based metallacrown complexes may be shown as Ln(III)[12-MC-4]$_2$[24-MC-8]. "MC" refers to the metallacrown macrocycle with a repeating sub-unit consisting of the transition metal ion (M(II)) and the hydroximate (HA) ligand.

The Ln(III) is a central ion that bonds (e.g., via coordination bonding) to the capping crowns, [12-MC-4]. It is to be understood that $Ln^{3+}$ may include any lanthanide ion, such as dysprosium ($Dy^{3+}$), ytterbium ($Yb^{3+}$), neodymium ($Nd^{3+}$), gadolinium ($Gd^{3+}$), terbium ($Tb^{3+}$), europium ($Eu^{3+}$), erbium ($Er^{3+}$), lanthanum ($La^{3+}$), cerium ($Ce^{3+}$), praseodymium ($Pr^{3+}$), promethium ($Pm^{3+}$), samarium ($Sm^{3+}$), holmium ($Ho^{3+}$), thulium ($Tm^{3+}$), or lutetium ($Lu^{3+}$). Throughout the application, the "$Ln^{3+}$", "Ln(III)", or "lanthanide" may be replaced with other rare-earth metal ions, such as yttrium ($Y^{3+}$) and scandium ($Sc^{3+}$). FIG. 1 illustrates the emission spectra of luminescent lanthanides. This figure clearly illustrates the sharp emission bands of each lanthanide, and that there is spectral discrimination among the various lanthanides.

The transition metal ion (TM(II)) may be selected from the group consisting of $Co^{2+}$, $Ni^{2+}$, $Cu^{2+}$, $Zn^{2+}$, $Rh^{2+}$, $Pd^{2+}$, $Ag^{2+}$, $Cd^{2+}$, $Ir^{2+}$, $Pt^{2+}$, $Au^{2+}$, or $Hg^{2+}$.

The HA ligand may be pyrazinehydroximate, quinoxalinehydroximate, quinaldinehydroximate, or combinations thereof. Pyrazinehydroximate (pyzHA) has the structure:

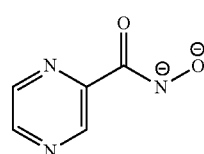

(Structure 1)

and is formed from the deprotonation of pyrazinehydroxamic acid:

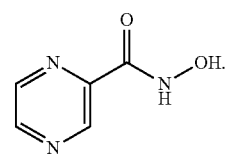

(Structure 2)

Similarly, quinoxalinehydroximate (quinoHA, not shown) is formed from the deprotonation of quinoxalinehydroxamic acid:

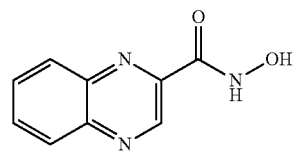

(Structure 3)

and quinaldinehydroximate (quinHA, not shown) is formed from the deprotonation of quinaldinehydroxamic acid (sometime referred to as quinaldichydroxamic acid):

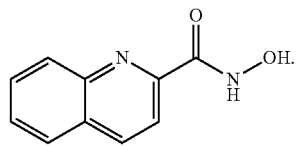

(Structure 4)

Derivatives of the previously listed hydroxamic acids (structures 2, 3, 4) may also be used to form suitable hydroximate ligands. For example, any combination of R-groups may be bound to positions 3, 5 and 6 in Structure 2, to positions 3 and 5-8 in Structure 3, and to positions 3-8 in Structure 4 above (where position 1 is the N atom at the top of the ring the numbered positions proceed to the right around the ring(s), and wherein the carbon atoms in Structures 3 and 4 that are shared between the two rings are not numbered). In an example, the R-groups are independently selected from —H, -D (deuterium), —OH, —SH, —NH$_2$, —NO$_2$, —F, —Cl, —Br, —I, —CF$_3$, —OCH$_3$, —SO$_3$H, —CH$_3$, and —CN. In another example, the R-group may also be a fused aromatic ring. Examples of the fused aromatic ring include benzene, naphthalene, phenanthrene, chrysene, or pyrene. It is to be understood that each position on the fused aromatic ring may also have R-groups bound thereto (e.g., —H, -D (deuterium), —OH, etc.). In yet a further example, the R-group at any of positions 3-8 of Structure 1 may also be a fused heterocyclic ring. Examples of the fused heterocyclic ring include furan, thiophene, pyrrole, pyridine, imidazole, thiazole, pyrimidine, indole, isoindole, indolizine, purine, carbazole, dibenzofuran, oxazole, or isoxazole. It is to be understood that each position on the fused heterocycle may also have R-groups bound thereto (e.g., —H, -D (deuterium), —OH, etc.). In still another example, the R-group(s) may be amides, or chromophoric or recognition regions, such as biotin, sugar, oligos, peptides (e.g., RGD), antibodies, or the like. In still other examples, the R groups may be =O, =N, —$N_3$, —NR'H, —$NR'_2$, —$NR'^{3+}$, —COOH, —COOR', —$CH_2$—R', —$CHR_2$, —CHR'R", —CR'R"R''', —OR', or the like, where R', R", and R''' may be independently selected from any of the aforementioned R-groups.

Examples of other derivatives include heterocycles derived from the hydroxamic acids with carbon (instead of nitrogen) at position 4 in Structures 2 and 3, or nitrogen, oxygen or sulfur (instead of carbon) at positions 3 to 8 in Structure 4. It is to be understood that these derivatives could contain nitrogen, oxygen or sulfur atoms individually or in combination at the various positions.

The HA ligands disclosed herein provide the complexes with a unique molecular structure. In addition, this ligand or a derivative thereof efficiently absorbs excitation light and transfers the resulting energy to the Ln(III) ion. It has been unexpectedly found that the metallacrown complexes formed with the HA ligand(s) or a derivative thereof provide a combination of a near-visible ligand-based charge transfer absorption, remarkably high quantum yields (exhibiting intense near-infrared luminescence), and long luminescence lifetimes. Complexes with these properties may be used in a variety of applications, including the example simultaneous cell staining and imaging methods disclosed herein.

Figure 30:
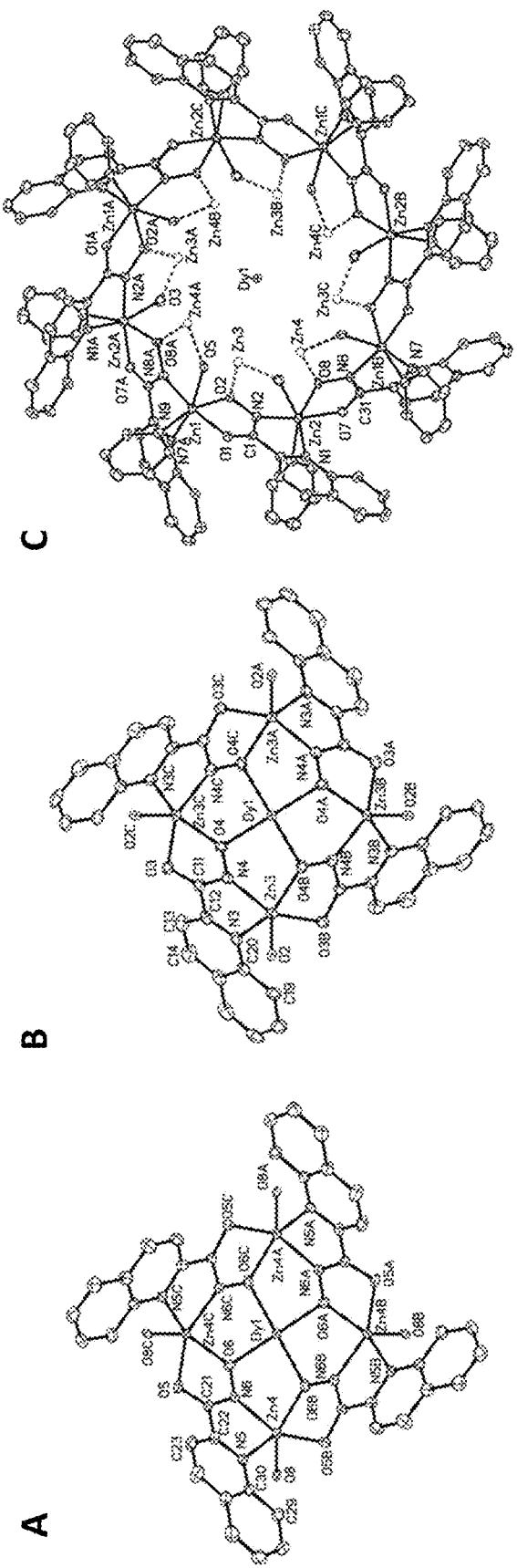
FIG. 30. Structures of [12-MC-4] and [24-MC-8] capping crowns. (A) Structure 5, (B) Structure 6; (C) Structure 7.

As mentioned above, the metallacrown complexes include the two capping crowns, [12-MC-4]. Example structures of the [12-MC-4] capping crowns are shown in FIGS. 30 (A) and (B), with 50% thermal displacement parameters and a partial numbering scheme.

Structures 5 and 6 illustrate the Ln(III) ion (in these examples Dy) bonded to the four inward-facing hydroximate oxygen atoms of each capping crown. In Structure 5, these inward-facing hydroximate oxygen atoms are labeled O6, O6A, O6B and O6C, and in Structure 6, these inward-facing hydroximate oxygen atoms are labeled O4, O4A, O4B and O4C. During the method of making the metallacrown complex (discussed below), the HA ligand cyclizes to form a repeating [M(II)HA] sub-unit, which in [12-MC-4], is repeated four times. As a result, each [12-MC-4] capping crown has twelve total atoms (e.g., 4 Zn, 4 O, and 4 N) in its macrocyclic ring.

The metallacrown complex also includes the encapsulating crown, [24-MC-8]. An example structure of the [24-MC-8] encapsulating crown is shown in FIG. 30 (C), with 50% thermal displacement parameters and a partial numbering scheme.

In this example, the HA ligand cyclizes to form the repeating [M(II)HA] sub-unit, which in [24-MC-8] is repeated eight times. As a result, each [24-MC-8] encapsulating crown has twenty-four total atoms (i.e., 8 Zn, 8 O, and 8 N) in its macrocyclic ring.

Structure 7 also illustrates the non-bonded central Ln(III) ion (e.g., Dy1). The dashed lines indicate how the central crown bridges to the smaller, concave, capping crowns (Structures 5 and 6).

The method used to form the metallacrown complex may utilize pyridine or some other solvent (e.g., dimethylformamide or methanol), and thus the encapsulating crown (Structure 7) may also have eight pyridine rings, or some other coordinating solvent molecules, attached thereto.

Figure 31:
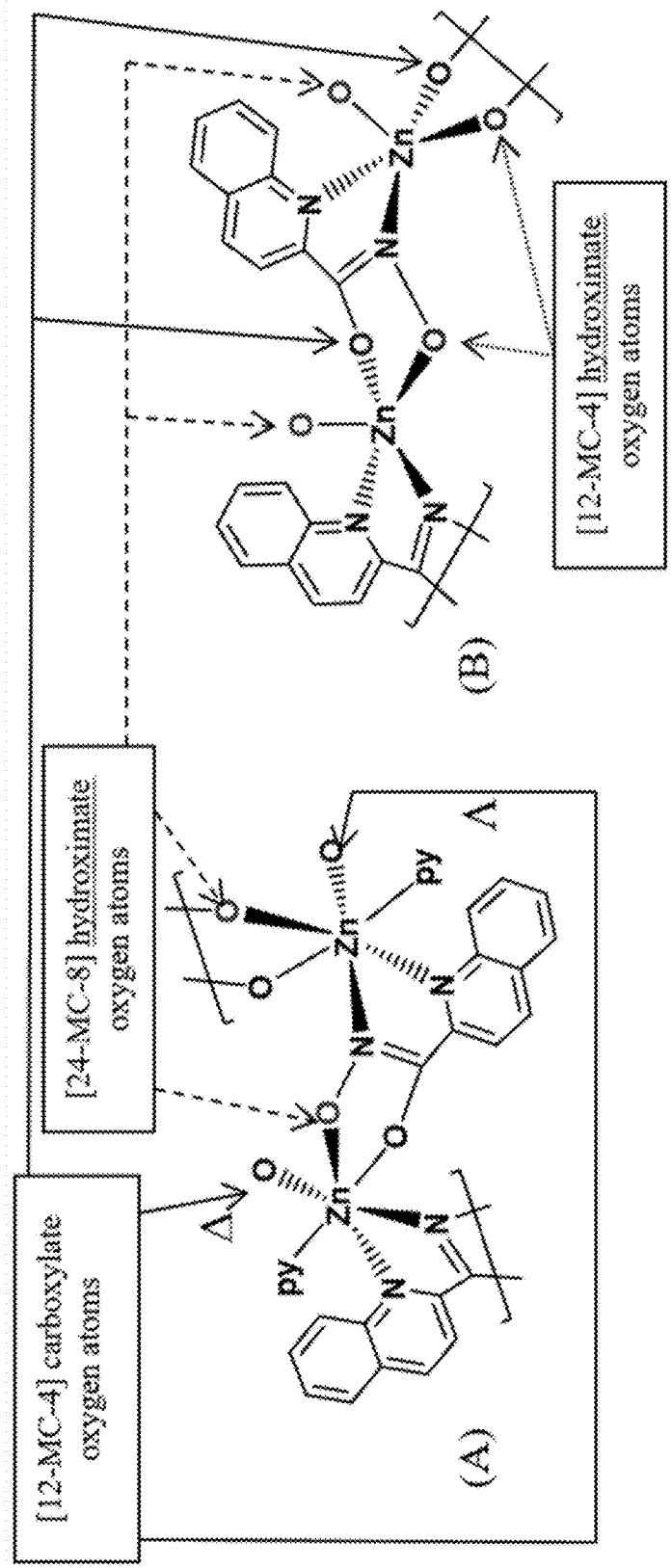
FIG. 31. Coordination geometry of $Zn^{2+}$ in [24-MC-8] (A) and in [12-MC-4] (B).

As mentioned above, the transition metal may be any divalent transition metal (II) ion. In the examples disclosed herein, $Zn^{2+}$ is the transition metal ion used. The coordination geometry of $Zn^{2+}$ in [24-MC-8] (A) and in [12-MC-4] (B) is shown in FIGS. 31 (A) and (B).

The coordination geometry of $Zn^{2+}$ indicates that the distinct metallacrown rings are linked through bridging oxygen atoms, namely the [12-MC-4] carboxylate oxygen atoms (identified with solid arrows) and the [24-MC-8] hydroximate oxygen atoms (identified with dashed arrows). In other words, the [24-MC-8] unit has a cavity at its center, and the sandwich complex formed between the $Ln^{3+}$ ion and the two [12-MC-4] units is bound within that cavity through the bridging oxygen atoms. As illustrated in (B) above, the $Ln^{3+}$ ion is bound to the [12-MC-4] hydroximate oxygen atoms (identified by dotted arrows).

A charge balance of the metallacrown complex that is formed may be obtained by the presence of a negatively charged species, such as an unbound counterion (e.g., triflate(s), mesylate(s), besylate(s), camsylate(s), edisylate(s), estolate(s), esylate(s), napsylate(s), tosylate(s), fluoride(s), chloride(s), bromide(s), iodide(s), nitrate(s), sulfate(s), carbonate(s), acetate(s), sulfonate(s), or phosphate(s)).

Specific examples of the Ln(III)$TM_{16}$(HA ligand)$_{16}$ metallacrown complexes include: [Ln(III)$Zn_{16}$(pyrazinehydroximate)$_{16}$(pyridine)$_8$] counter ion; [Ln(III)$Zn_{16}$(quinoxalinehydroximate)$_{16}$(pyridine)$_8$] counter ion; or [Ln(III)$Zn_{16}$(quinaldinehydroximate)$_{16}$(pyridine)$_8$] counter ion. As another example, the Ln(III)$TM_{16}$(HA ligand)$_{16}$ metallacrown complex may be a mixed ligand metallacrown complex, with at least two different HA ligands. When mixed ligand metallacrown complexes are formed, the result may be a mixture of metallacrown complexes, where each species in the metallacrown mixture is [Ln(III)$TM_{16}$(HA ligand 1)$_x$(HA ligand 2)$_y$(pyridine)$_8$] counter ion, wherein x+y=16, and wherein preferably x ranges from 8 to 13, and thus y ranges from 8 to 3. As a more specific example, the mixture may include [Ln(III)$Zn_{16}$(pyrazinehydroximate)$_x$(quinoxalinehydroximate)$_y$(pyridine)$_8$] counter ion, where the predominant species is x=12 and y=4 (e.g., [Nd(III)$Zn_{16}$(pyrazinehydroximate)$_{12}$(quinoxalinehydroximate)$_4$(pyridine)$_8$] ($CF_3SO_3$)), but other species (in which x=13 and y=3, and x=11 and y=5) may also be present.

In an example of the method for making the lanthanide-based metallacrown complex, an example of a hydroxamic acid precursor of the HA ligand, a transition metal salt, and a rare-earth metal salt are dissolved in a solvent to form a solution. In another example of the method for making the lanthanide-based metallacrown complex, the hydroxamic acid precursor of the HA ligand is dissolved in the solvent to form a solution, and then the transition metal salt and the rare-earth metal salt are added. Example solvents include dimethylformamide (DMF), methanol, pyridine, water, and combinations thereof.

The hydroxamic acid precursor of the HA ligand may be prepared in a single step. In an example, fresh hydroxylamine is first prepared by combining hydroxylamine hydrochloride and potassium hydroxide in methanol at about 0° C.

This solution may be stirred (e.g., for about 20 minutes or longer) and filtered to remove potassium chloride. Quinaldic acid and N-methylmorpholine are combined with stirring in dichloromethane. This solution may be cooled to about 0° C., at which time ethylchloroformate is added. This reaction may be stirred for about 20 minutes to 1 hour, and then filtered. The hydroxylamine solution is added to the filtrate at about 0° C. This reaction mixture may be allowed to warm to room temperature and stirred for about 1.5 hours. The volume may then be reduced to about 200 mL en vacuo and water is added to induce the precipitation of a white solid. The solid is collected by filtration, and may be triturated with hot (about 40° C.) dichloromethane to yield quinaldichydroxamic acid as a white powder. The hydroxamic acid may be used in the synthesis of the MC complexes. During the synthesis, the hydroxamic acid will undergo deprotonation.

Any transition metal salt may be used. In an example, the transition metal salt is a triflate (-Otf), a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a sulfonate, or a phosphate of any of $Co^{2+}$, $Ni^{2+}$, $Cu^{2+}$, $Zn^{2+}$, $Rh^{2+}$, $Pd^{2+}$, $Ag^{2+}$, $Cd^{2+}$, $Ir^{2+}$, $Pt^{2+}$, $Au^{2+}$, or $Hg^{2+}$.

The rare-earth metal salt may be a triflate, a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a sulfonate, or a phosphate of any of $Y^{3+}$, $Sc^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, or $Lu^{3+}$.

As mentioned above, in some examples of the method, the precursor to the HA ligand, the transition metal salt, and the rare-earth metal salt are dissolved in the solvent to form a solution. This example method may be suitable when quinaldinehydroxamic acid is used as the precursor to the HA ligand. In this example method, a base is then added to the solution. Examples of suitable bases include triethylamine (TEA), trimethylamine, or other Brønsted bases. In an example, when the base is added to the solution, the resulting reaction mixture turns yellow.

In this example method, the reaction mixture (i.e., the solution and the base) is then stirred for a predetermined time at a predetermined temperature. In an example, the temperature is room temperature (e.g., from about 18° C. to about 22° C.) and the time ranges from about 12 hours to about 24 hours.

The reaction mixture is then exposed to a purification method to produce the highly pure metallacrown complex. Examples of suitable purification methods include recrystallization by slow evaporation of the solvent, recrystallization by vapor diffusion, recrystallization by solvent layering, high-performance liquid chromatography (HPLC), or flash chromatography. In one example, pyridine is used in the purification process, which results in the introduction of pyridine ligands to the metallacrown complex.

Also as mentioned above, in some other examples of the method, the precursor to the HA ligand is dissolved in the solvent to form a solution. This example method may be suitable when pyrazinehydroxamic acid and/or quinoxalinehydroxamic acid are used as the precursor(s) to the HA ligand(s).

In this example method, the HA ligand is dissolved in the solvent to form a solution. The solution may be stirred in order to completely dissolve the solid. The transition metal salt and the rare-earth metal salt may then be added to the solution. The solution may be stirred at room or an elevated temperature) for a predetermined amount of time, and then filtered.

The following are three examples of this example of the method:

Synthesis of $[Zn_{16}Ln(pyzHA)_{16}(py)_8](OTf)_3$

Pyrazinehydroxamic acid (45.0 mg, 0.32 mmol) is added into a solution containing 1.0 mL pyridine and 10.0 mL water. The solution is stirred for about 5 minutes to completely dissolve the solid. Zinc triflate (116.0 mg, 0.32 mmol) and Lanthanide triflate (0.04 mmol) are added, and the yellow solution is stirred for about 5 minutes at room temperature and then filtered. The filtrate may be left undisturbed in order to yield yellow crystals after three days. The crystals may be collected by filtration and dried in air.

Synthesis of $[Zn_{16}Ln(quinoHA)_{16}(py)_8](OTf)_3$

Quinoxalinehydroxamic acid (60.5 mg, 0.32 mmol) is added into a solution containing 1.0 mL pyridine, 5.0 mL DMF, and 5.0 mL water. The solution is stirred for about 5 minutes to completely dissolve the solid. Zinc triflate (116 mg, 0.32 mmol) and Lanthanide triflate (0.04 mmol) are added, and the orange solution is stirred at 80° C. for about 2 hours, cooled down to room temperature, and then filtered. The filtrate may be left undisturbed to yield red crystals after one week. The crystals may be collected by filtration, washed with water, and dried in air.

Synthesis of $[Zn_{16}Ln(pyzHA)_x(quinoHA)_y(py)_8](OTf)_3$

Pyrazinehydroxamic acid (37.5 mg, 0.27 mmol) and Quinoxalinehydroxamic acid (17.0 mg, 0.09 mmol) are added into a solution containing 1.0 mL pyridine and 5.0 mL water. The solution is stirred for 5 minutes to completely dissolve the solids. Zinc triflate (131.0 mg, 0.36 mmol) and Lanthanide triflate (0.045 mmol) are added and the orange solution is stirred at room temperature for about 20 minutes, and then filtered. The filtrate may be left undisturbed to yield a mixture of yellow/red crystals after one week. The crystals are collected by filtration, washed with water, and dried in air.

The metallacrown complex may be used in examples of the methods disclosed herein. One example method is for simultaneously counter staining and fixing of cells and another example method is an optical imaging method for necrotic cells.

In an example of the method for simultaneously staining and fixing cells, the cells may first be obtained and prepared. Examples of suitable cells include human epithelial cervix carcinoma (HeLa) cells, mesenchymal stem cells (MSC), or other suitable cells. Preparation of the cells may involve seeding and culturing the cells. It is to be understood that the cell culture medium selected may vary, depending upon the cell line that is utilized. The cells may be washed with fresh medium.

Throughout the steps of the method, at least some of the cells (e.g., at least 90%), and in many instances, all of the cells, undergo necrosis (unprogrammed cell death) These cells may also be a combination of necrotic cells and apoptotic cells.

The cells are incubated (initially) in a solution including the $Ln(III)TM_{16}(HA\ ligand)_{16}$ metallacrown complex(es) in a medium. Throughout the discussion of this example method, the $Ln(III)TM_{16}(HA\ ligand)_{16}$ metallacrown complex will be referred to as the $Ln^{3+}[Zn(II)MC_{HA}]$ metallacrown complex(es). It is to be understood that the medium selected may vary, depending upon the cell line that is utilized. The medium may be a serum-supplemented reduced medium (such as OPTI-MEM® media supplemented with fetal bovine serum (FBS)). The concentration of the $Ln^{3+}[Zn(II)MC_{HA}]$ metallacrown complex in the solution may range from about 45 μM to about 400 μM. As specific examples, the concentration of the $Ln^{3+}[Zn(II)MC_{HA}]$ metallacrown complex of the solution may be about 45 μM, 150 μM or 200 μM.

The initial incubation may take place for a predetermined time, depending on the cell line and metallacrown complex that are used. The initial incubation time (T1) may range from about 10 minutes to about 3 hours. As examples, a metallacrown complex formed with $Yb^{3+}$ and with $Nd^{3+}$ may be initially incubated for about 15 minutes.

During the initial incubating period, at least some of the cells may die. The percentage of cells that die during this point of the method may depend upon the concentration of the $Ln^{3+}[Zn(II)MC_{HA}]$ metallacrown complex and the initial incubation time (T1). When the initial incubation time (T1) is less than 24 hours, and the concentration ranges from about 2.5 μM to about 100 μM, up to 10% of the cells may die.

The incubating cells are then exposed to UV light. In an example, the UV light is UV-A light. UV light exposure may take place for a time (T2) ranging from about 5 minutes to about 10 minutes. The short exposure to UV light, in combination with the high concentration of the $Ln^{3+}[Zn(II)MC_{pyzHA}]$ metallacrown complex brings about a photochemical effect, which is similar to cell fixation that may be obtained using formaldehyde or methanol.

After UV light exposure, the cells are allowed to continue to incubate in the solution. In an example, the continued incubation of the cells in the solution occurs for a time (T3) ranging from about 1 hour to about 2 hours. Continued cell incubation after UV light exposure allows the $Ln^{3+}[Zn(II)MC_{HA}]$ metallacrown complex to stain the nucleus and the cytoplasm of at least some (if not all) of the fixed cells.

In some examples of the method, the incubating cells are not exposed to any additional UV light. In some other examples of the method, the incubating cells may be exposed to additional UV light for a time (T4) ranging from about 1 minute to about 5 minutes.

After continued incubation, and if performed, additional UV light exposure, the stained and fixed cells may be washed (e.g., with fresh medium). The simultaneously stained and fixed cells may be an optical imaging technique, such as epifluorescence microscopy, confocal microscopy, or combinations therefore.

An example of the optical imaging method disclosed herein includes forming the simultaneously fixed and stained cells via the method disclosed herein, and exposing the simultaneously fixed and stained cells to the optical imaging technique.

To further illustrate the present disclosure, examples are given herein. It is to be understood that these examples are provided for illustrative purposes and are to be construed as non-limiting.

EXAMPLES

In the following examples, $Yb^{3+}[Zn(II)MC_{pyzHA}]$ complexes (which can also be described as $YbZn_{16}(pyz)_{16}MC$), $Nd^{3+}[Zn(II)MC_{pyzHA}]$ (which can also be described as $NdZn_{16}(pyz)_{16}MC$) complexes, or $Nd^{3+}[Zn(II)MC_{(pyzHA)x(quinoHA)y}]$ ($NdZn_{16}(pyz)_x(quino)_yMC$) complexes are utilized. The respective complexes were formed by the following procedures:

Synthesis of $Yb^{3+}[Zn(H)MC_{pyzHA}]$ Complex or $Nd^{3+}[Zn(II)MC_{pyzHA}]$ Complex Pyrazinehydroxamic acid (45.0 mg, 0.32 mmol) was added into a solution containing 1.0 mL pyridine and 10.0 mL $H_2O$. The solution was stirred for 5 minutes to completely dissolve the solid. Zinc triflate (116.0 mg, 0.32 mmol) and Ytterbium triflate or Neodymium triflate (0.04 mmol) were added, and the yellow solution was stirred for 5 minutes at room temperature and then filtered. The filtrate was left undisturbed to give yellow crystals after three days. The crystals were collected by filtration and dried in air.

Synthesis of $Nd^{3+}[Zn(II)MC_{(pyzHA)x(quinoHA)y}]$ Complex

Pyrazinehydroxamic acid (37.5 mg, 0.27 mmol) and Quinoxalinehydroxamic acid (17.0 mg, 0.09 mmol) were added into a solution containing 1.0 mL pyridine and 5.0 mL $H_2O$. The solution was stirred for 5 minutes to completely dissolve the solids. Zinc triflate (131.0 mg, 0.36 mmol) and Neodymium triflate (0.045 mmol) were added, and the orange solution was stirred at room temperature for 20 minutes and then filtered. The filtrate was left undisturbed to give a mixture of yellow/red crystals after one week. The crystals were collected by filtration, washed with $H_2O$, and dried in air.

Figure 2:
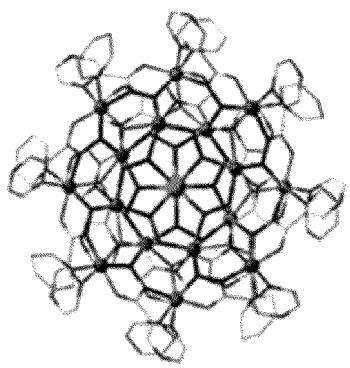
FIG. 2 illustrates an x-ray crystallographic representation of $Yb^{3+}[Zn(II)MC_{pyzHA}]$ complex, and the pyrazinehydroxamic acid ($H_2pyzHA$) from which it was formed.
Figure 2:
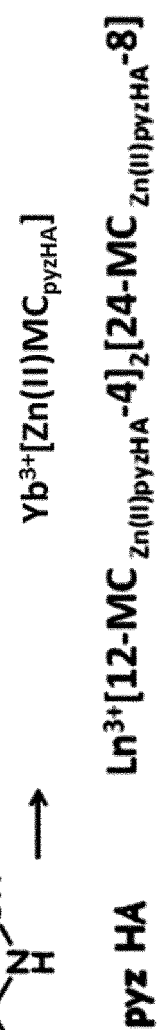
Figure 3:
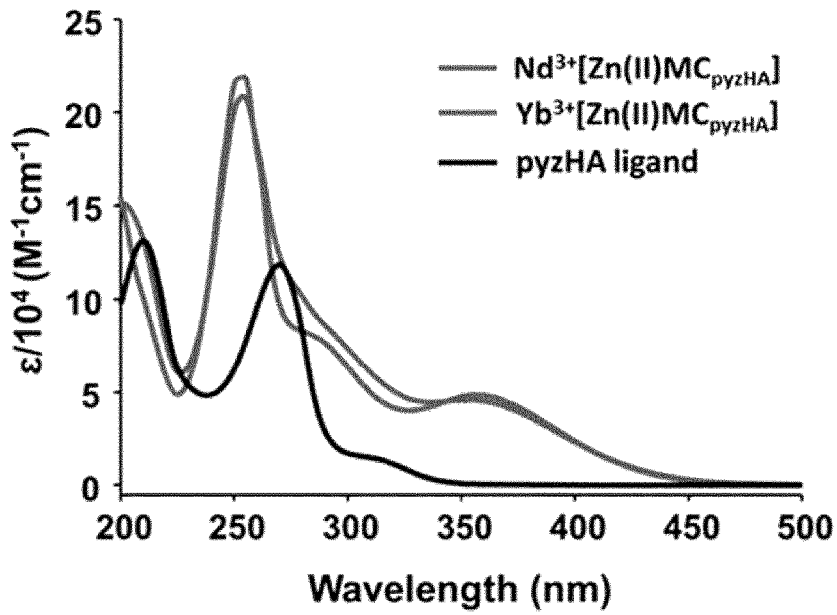
FIG. 3. illustrates the absorption spectra of $H_2pyzHA$ (multiplied by a factor of 16), $Yb^{3+}[Zn(II)MCpyzHA]$ and $Nd^{3+}[Zn(II)MCpyzHA]$ MCs in water (150 µM, room temperature).

In several of the following examples, $Yb^{3+}[Zn(II)MC_{pyzHA}]$ complexes were formed. The left side of FIG. 2 illustrates pyrazinehydroxamic acid. The right side of FIG. 2 is a representation of the metallacrown structure (as obtained from X-Ray structure) which is formed by the supramolecular assembly of the hydroxamic acid units (which form the pyz HA ligands) with zinc and ytterbium salts in a controlled ratio. The $Yb^{3+}[Zn(II)MC_{pyzHA}]$ complex has a unique and rigid structure where the lanthanide ion is positioned in the center of the structure (turquoise sphere) and surrounded with zinc (grey spheres).

Figure 4:
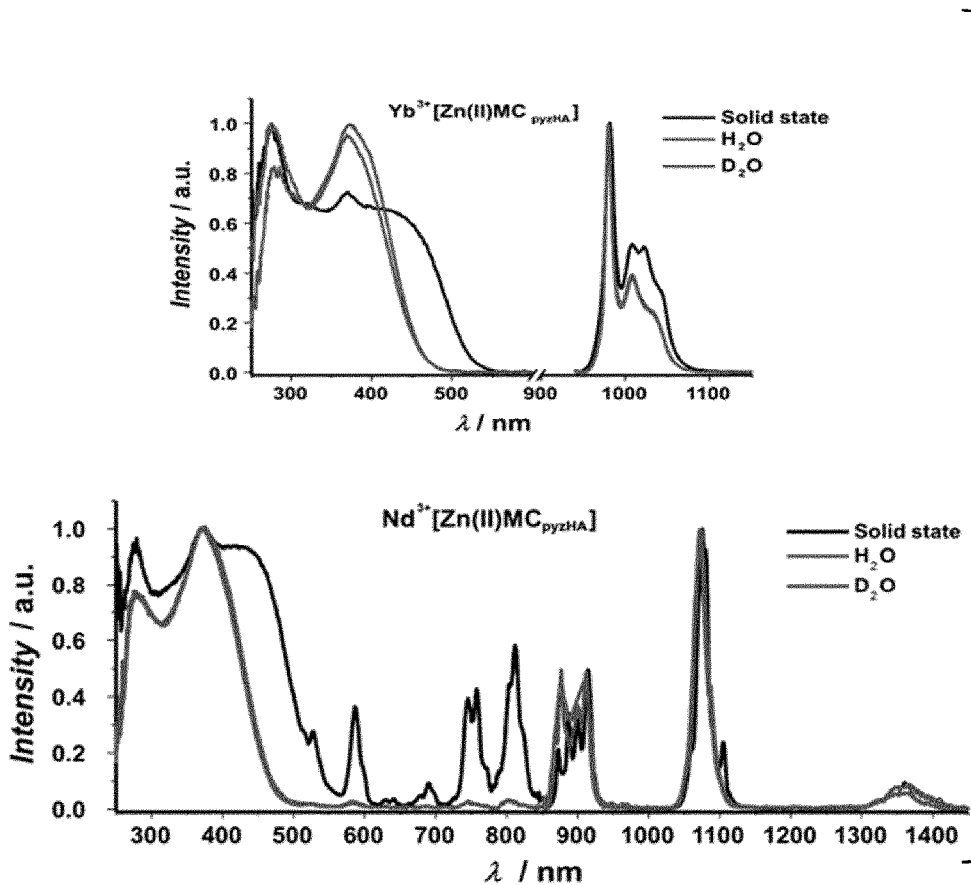
FIG. 4. illustrates the normalized excitation ($\lambda_{em}(Nd^{3+})$= 1070 nm, $\lambda_{em}(Yb^{3+})$=980 nm) and emission ($\lambda_{ex}$=370 nm) spectra of $Yb^{3+}[Zn(II)MC_{pyzHA}]$, at the top, and $Nd^{3+}[Zn(II)MC_{pyzHA}]$ MCs, at the bottom, (solid or 200 µM solutions, room temperature)
Figure 5:
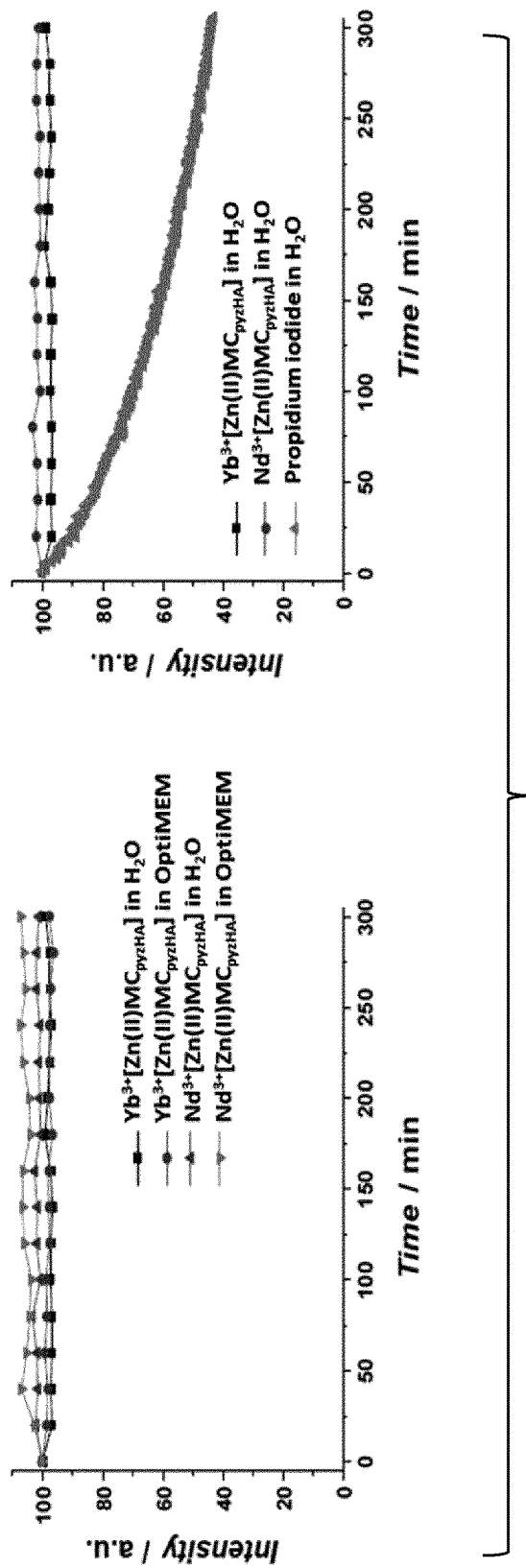
FIGS. 5. (A) and (B) are graphs illustrating the photostability of the $Yb^{3+}[Zn(II)MC_{pyzHA}]$, the $Nd^{3+}[Zn(II)MC_{pyzHA}]$, and/or propidium iodide in different media.

The structure of $Yb^{3+}[Zn(II)MC_{pyzHA}]$ complex and other MC complexes provide sensitization and protection to the luminescent lanthanides. These metallacrowns exhibit promising photophysical properties which are among the highest values for quantum yields and luminescence lifetimes. As will be illustrated in the following examples, several of the MC complexes have demonstrated remarkable NIR luminescence properties (some of which show the highest luminescence quantum yield values reported to date for selected NIR emitting lanthanides ($Yb^{3+}$, $Nd^{3+}$)). As shown in FIG. 4 (Top), metallacrowns formed with ytterbium can be excited up to 480 nm. As will be illustrated in several of the following examples, these metallacrowns demonstrated intense near-infrared signals in cancer cells for good signal to noise ratio and high sensitivity of detection.

Example 1—NIR Epifluorescent Microscopy of the $Yb^{3+}[Zn(II)MC_{pyzHA}]$ Complex with HeLa Cancer Cells or Mesenchymal Stem Cells (MSC)

Experimental Conditions

HeLa (Human Epithelial Cervix Carcinoma) cell line, obtained from ATCC (Molsheim, France), was cultured in Dulbecco's modified Eagle's medium (DMEM) supplemented with 10% heat-inactivated fetal bovine serum (FBS), 1% of 100× non-essential aminoacid solution, 1% of L-glutamine (GlutaMAX) and 1% of streptomycin/penicillin antibiotics. Cells were seeded in a 8-well Lab Tek Chamber coverglass (Nunc, Dutsher S.A., Brumath, France) at a density of $6 \times 10^4$ cells/well and cultured at 37° C. in 5% humidified $CO_2$ atmosphere.

The MSC (Mesenchyml Stem Cells) cell line was obtained from University in Orleans, 13MTO Laboratory (Orleans, France). The as-received MSC cell line has been obtained from the bone marrow of rats. The MSC cell line was cultured in Minimum Essential Medium (MEM) supplemented with 10% heat-inactivated fetal bovine serum (FBS), 1% of L-glutamine (GlutaMAX) and 1% of streptomycin/penicillin antibiotics. The MSC were also seeded in a similar manner to the HeLa cells.

After 24 hours, the respective cell culture media was removed and the HeLa cells or MSC were incubated with the $Yb^{3+}[Zn(II)MC_{pyzHA}]$ complex according to one of the following procedures.

Long Incubation, No UV Light Exposure:

Some of HeLa cells were washed twice with OPTI-MEM® media (room temperature), and were incubated with a solution of 150 μM $Yb^{3+}[Zn(II)MC_{pyzHA}]$ complex in OPTI-MEM® media (supplemented with 2% of FBS at 37° C. in 5% $CO_2$ atmosphere) for 12 hours.

Short Incubation, UV Light Exposure #1:

Some of the HeLa cells were washed twice with OPTI-MEM® media (room temperature), incubated with a solution of 150 μM $Yb^{3+}[Zn(II)MC_{pyzHA}]$ complex in OPTI-MEM® media (supplemented with 2% of FBS at 37° C. in 5% $CO_2$ atmosphere) for 15 minutes, illuminated with UV light (377 nm) for 8 minutes, and then were allowed to continue incubating for 1 hour. The continued incubation enabled the internalization of the complexes.

Short Incubation, No UV Light Exposure:

Some of HeLa cells were washed twice with OPTI-MEM® media (room temperature), and were incubated with a solution of 45 μM $Yb^{3+}[Zn(II)MC_{pyzHA}]$ complex in OPTI-MEM® media (supplemented with 2% of FBS at 37° C. in 5% $CO_2$ atmosphere) for 15 minutes.

All of the previously mentioned incubated HeLa cells were then washed with fresh OPTI-MEM® media and were incubated with 3 μM propidium iodide for 5 minutes. Propidium iodide is a commercially available stain (emitting in the visible range) for necrotic cells, and was used to confirm cell necrosis.

Short Incubation, UV Light Exposure #2:

Some of the HeLa cells were washed twice with OPTI-MEM® media (room temperature), incubated with a solution of 150 μM $Yb^{3+}[Zn(II)MC_{pyzHA}]$ complex in OPTI-MEM® media (supplemented with 2% of FBS at 37° C. in 5% $CO_2$ atmosphere) and 3 μM propidium iodide for 5 minutes, illuminated with UV light (377 nm) for 5 minutes, and then were allowed to continue incubating for 1 hour. The continued incubation enabled the internalization of the complexes.

Short Incubation, UV Light Exposure #3:

The MSC cells were incubated with a solution of 150 μM $Yb^{3+}[Zn(II)MC_{pyzHA}]$ complex in OPTI-MEM® media (supplemented with 2% of FBS at 37° C. in 5% $CO_2$ atmosphere) for 15 minutes, illuminated with UV light (377 nm) for 8 minutes, and then were allowed to continue incubating for 1 hour.

Prior to epifluorescent imaging, the HeLa and the MSC cells were washed twice with OPTI-MEM® (room temperature) in order to remove any non-specifically bound $Yb^{3+}[Zn(II)MC_{pyzHA}]$ complex. The cells were observed with a Zeiss Axio Observer Z1 fluorescence inverted microscope (Zeiss, Le Pecq, France) equipped with an EMCCD Evolve 512 (Roper Scientific) photometric camera or ORCA-R2 high resolution CCD camera. The light source, Zeiss HXP 120, was combined with the following filter cubes:

i. 377 nm with 50 nm band-pass filter with 50 nm bandwidth for the excitation and 805 nm long-pass filter 805 nm or 996 nm band-pass filter with 70 nm bandwidth for YbIII emission in the NIR range.

ii. 44780 nm band-pass filter with 650 nm bandwidth for the excitation and 805 nm long-pass filter 805 nm or 996 nm band-pass filter with 70 nm bandwidth for YbIII emission in the NIR range.

Experimental Results

Figure 18:
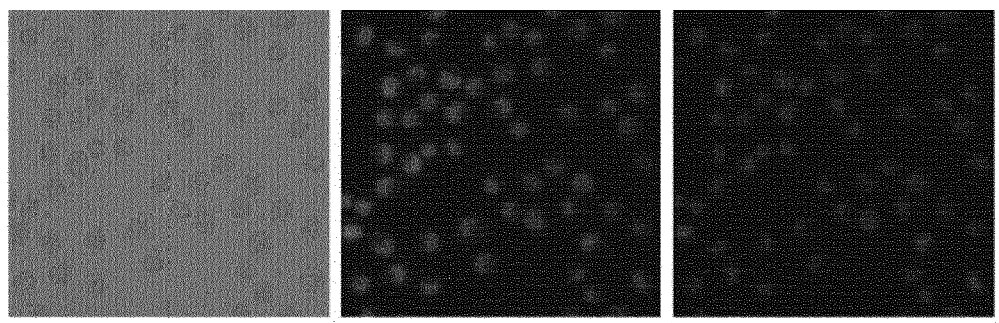
FIG. 18. (A) to (E) illustrate results of NIR epifluorescence microscopy (40× magnification), of HeLa cells incubated with 150 μM of Yb$^{3+}$[Zn(II)MC$_{pyzHA}$] for 12 hours, washed with OPTI-MEM® media and incubated with 3 μM propidium iodide for 5 minutes. (A) is the brightfield image; (B) is the image of emission signal arising from Yb$^{3+}$[Zn(II)MC$_{pyzHA}$] in the NIR range ($\lambda_{em}$=805 nm long pass filter) obtained after 8 s of exposure to excitation ($\lambda_{ex}$=447 nm band pass filter with 60 nm bandwidth); (C) is visible signal arising from propidium iodide obtained after 80 ms of exposure time ($\lambda_{em}$=605 nm band pass filter with 70 nm bandwidth and $\lambda_{ex}$=550 nm band pass filter with 25 nm bandwidth); (D) is (B) and (C) merged together; and (E) is (A), (B) and (C) merged together.
Figure 18:
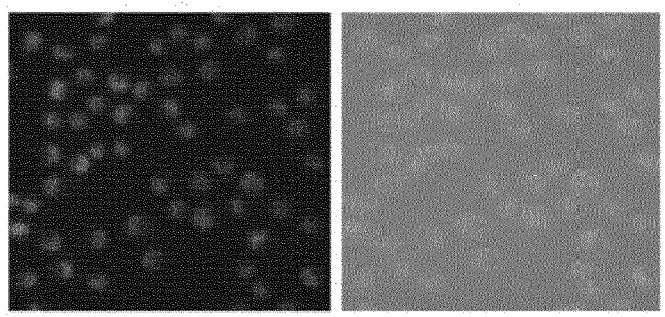

The results shown in FIG. 18. (A)-(E) are for the cells with the long incubation and no UV light exposure. The results in FIG. 18 (B) indicate that the incubation of HeLa cancer cells with $Yb^{3+}[Zn(II)MC_{pyzHA}]$ leads to cell death. From these results, it can be concluded that the MC is toxic to the HeLa cell line at the 150 μM concentration for incubation during 12 hours. Cell death was confirmed by incubation with propidium iodide (PI), as shown in FIG. 18 (C). As illustrated in the merged figures (FIGS. 18 (D) and (E), $Yb^{3+}[Zn(II)MC_{pyzHA}]$ and PI colocalize in the same cell compartment, and the signal was observed in the NIR region (Fig. (B)) and VIS region (Fig. (C)) originating from MC and PI, respectively.

Figure 9:
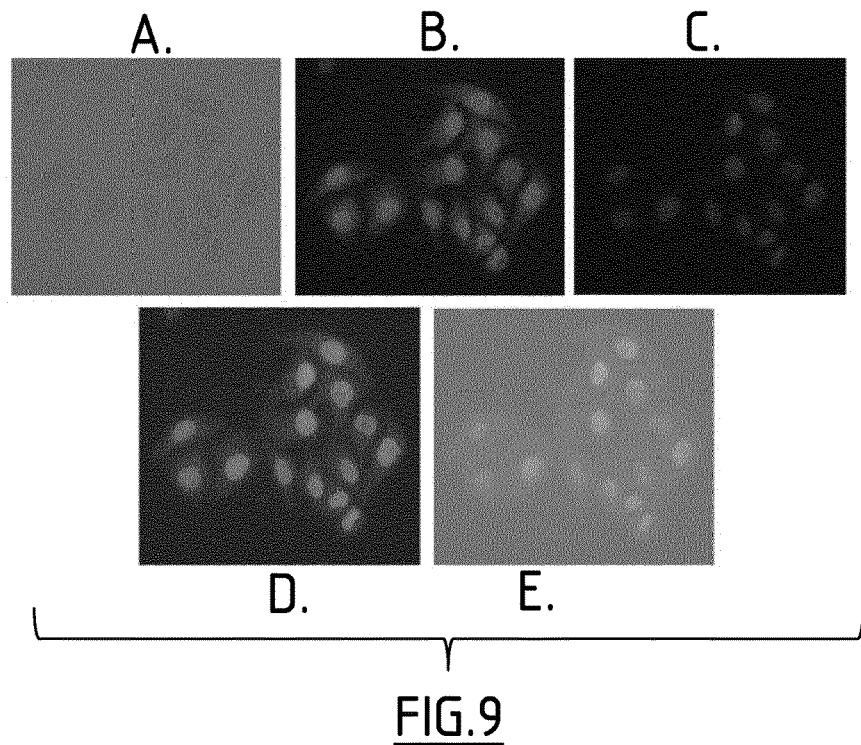
FIG. 9 (A)-(E) are images (40× magnification), obtained using NIR epifluorescence microscopy, of HeLa cells incubated with 150 µM of $Yb^{3+}[Zn(II)MC_{pyzHA}]$ for 15 minutes, illuminated with UV light (377 nm band pass filter with 50 nm bandwidth) for 8 minutes, further incubated for 1 hour, washed with OPTI-MEM® media and incubated with 3 µM propidium iodide for 5 minutes. (A) is the brightfield image; (B) is the image of the emission signal arising from $Yb^{3+}$ $[Zn(II)MC_{pyzHA}]$ in the NIR range ($\lambda_{em}$=805 nm, longpass filter) obtained after 8 s of exposure to excitation ($\lambda_{ex}$=447 nm, band pass filter with 60 nm bandwidth); (C) shows the image of the visible signal arising from propidium iodide obtained after 800 ms of exposure time ($\lambda_{em}$=605 nm, band pass filter with 70 nm bandwidth; and $\lambda_{ex}$=550 nm, band pass filter with 25 nm bandwidth); (D) is (B) and (C) merged together; and (E) is (A), (B), and (C) merged together.
Figure 10:
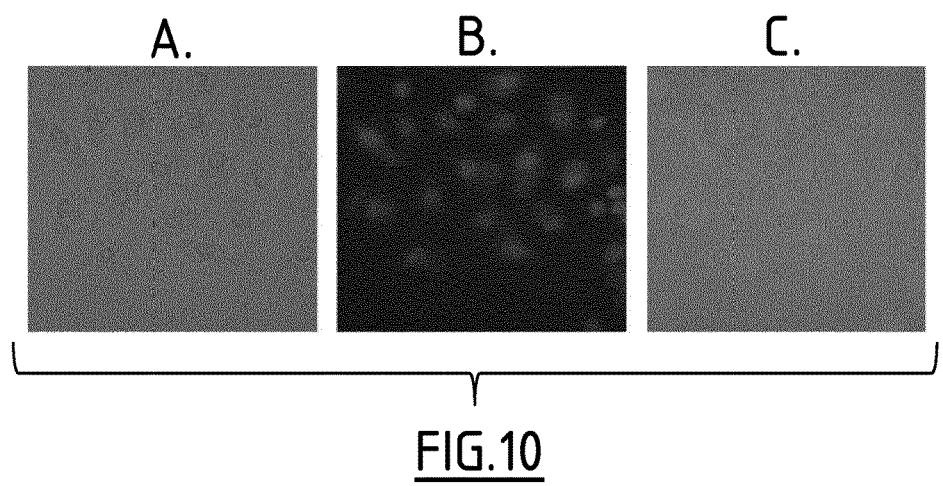
FIG. 10. (A) through (C) are images (40× magnification), obtained using NIR epifluorescence microscopy, of HeLa cells incubated with 150 µM $Nd^{3+}[Zn(II)MC_{pyzHA}]$ for 15 minutes, illuminated with UV light (377 nm) for 5 minutes, further incubated for 1 hour, washed with OPTI-MEM® media. (A) is the brightfield image; (B) is the image of the emission signal arising from $Nd^{3+}[Zn(II)MC_{pyzHA}]$ in the NIR range ($\lambda_{em}$=805 nm, longpass filter) obtained after 12 s of exposure to excitation ($\lambda_{ex}$=377 nm, band pass filter with 50 nm bandwidth); and (C) illustrates the merging of (A) and (B)
Figure 11:
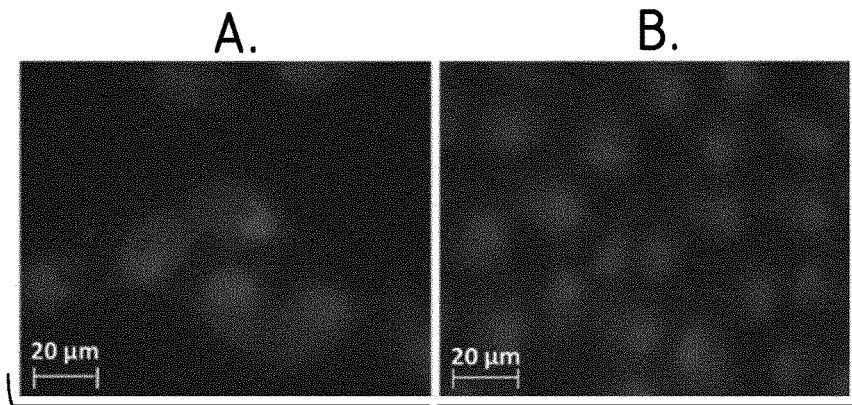
FIGS. 11. (A) and (B) illustrate results of epifluorescence microscopy experiments performed on HeLa cells fixed with $Yb^{3+}[Zn(II)MC_{pyzHA}]$. Detection of the NIR emission with a standard CCD camera (Orca-R2, Hamamatsu): (A)) $\lambda_{ex}$: 447 nm band pass filter with 60 nm bandwidth, $\lambda_{em}$: 805 nm longpass filter, exposure time: 30 s, (B) $\lambda_{ex}$: 447 nm band pass filter with 60 nm bandwidth, $\lambda_{em}$: 996 nm band pass filter with 70 nm bandwidth, exposure time: 80 s. 63× objective.
Figure 12:
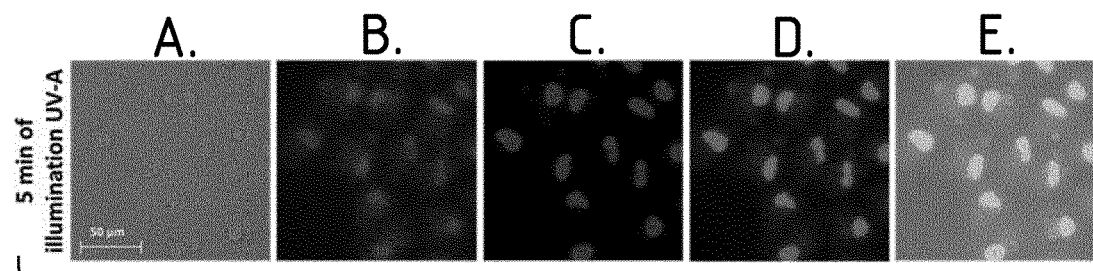
FIG. 12 (A) to (E) illustrate results of epifluorescence microscopy experiments on HeLa cells fixed with 150 μM Yb$^{3+}$[Zn(II)MC$_{pyzHA}$] and illumination with the UV-A light obtained through a 377 nm band pass filter (50 nm bandwidth) for 5 min. After fixation, the cells were washed and incubated with 3 μM PI for 5 min. (A) Brightfield. (B) NIR signal arising from Yb$^{3+}$[Zn(II)MC$_{pyzHA}$] ($\lambda_{ex}$: 447 nm band pass filter with 60 nm bandwidth, $\lambda_{em}$: 805 nm longpass filter, exposure time: 8 s). (C) Visible signal arising from PI ($\lambda_{ex}$: 550 nm band pass filter with 25 nm bandwidth, $\lambda_{em}$: 605 nm band pass filter with 70 nm bandwidth, exposure time: 800 ms). (D) Merged image obtained by the combination of the PI and Yb$^{3+}$[Zn(II)MC$_{pyzHA}$] images. (E) Merged image obtained by the combination of the PI, Yb$^{3+}$[Zn(II)MC$_{pyzHA}$] and brightfield images. 63× objective.

The results shown in FIG. 9, (A)-(E) are for the cells with the short incubation and UV light exposure #1. While not shown, the NIR signal arising from $Yb^{3+}[Zn(II)MC_{pyzHA}]$ was obtained using epifluorescent imaging one month after the procedure for counter staining and fixing was performed. The results after one month were compared with FIG. 9, (B) (the NIR signal right after the staining and fixing method was performed), and the comparison illustrated that the stained and fixed cells maintained the same shape and morphology. With this experiment, a new photochemical phenomenon arising from the exposure of HeLa cancer cells to UV-A light (377 nm) combined with the incubation of a high concentration of $Yb^{3+}[Zn(II)MC_{pyzHA}]$ was observed. This effect was similar to cell fixation obtained classically with formaldehyde or methanol. FIG. 9, (B) also illustrates that $Yb^{3+}[Zn(II)MC_{pyzHA}]$ operates as a NIR stain for the nucleus as well as for the cytoplasm of fixed HeLa cancer cells. The cell death was confirmed with the commercially available marker, propidium iodide (PI) (FIG. 9, (B)). As illustrated in the merged figures (FIGS. 9, (D) and (E)), $Yb^{3+}[Zn(II)MC_{pyzHA}]$ and PI colocalize in the same cell compartments, and the signal was observed in the NIR region (FIG. 9, (B)) and VIS region (FIG. 9, (C)) originating from MC and PI, respectively.

Figure 7:
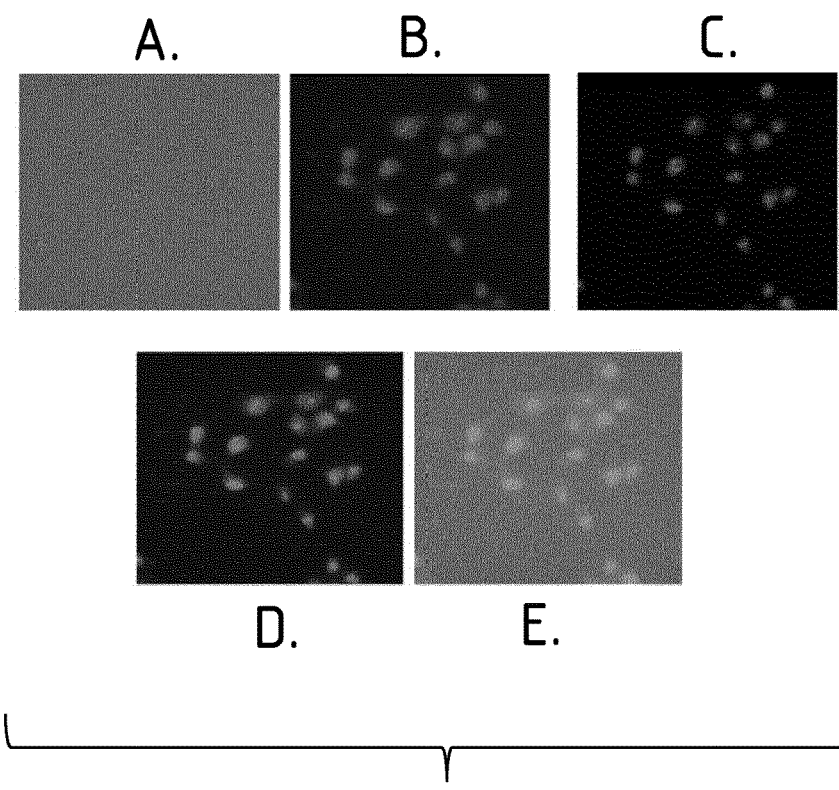
FIG. 7. (A)-(E) are images (40× magnification), obtained using NIR epifluorescence microscopy, of HeLa cells incubated with 45 µM of $Yb^{3+}[Zn(II)MC_{pyzHA}]$ for 15 minutes, washed with OPTI-MEM® media and incubated with 3 µM propidium iodide for 5 minutes. (A) is the brightfield image; (B) is the image of the emission signal arising from $Yb^{3+}$ $[Zn(II)MC_{pyzHA}]$ in the NIR range ($\lambda_{em}$=805 nm long pass filter) obtained after 10 s of exposure to excitation ($\lambda_{ex}$=447 nm, filter with 60 nm bandwidth); (C) shows visible signal arising from propidium iodide obtained after 100 ms of exposure time ($\lambda_{em}$=605 nm, band pass filter with 70 nm bandwidth; and $\lambda_{ex}$=550 nm, band pass filter with 25 nm bandwidth); (D) shows the merging of (B) and (C); and (E) shows the merging of (A), (B) and (C)
Figure 8:
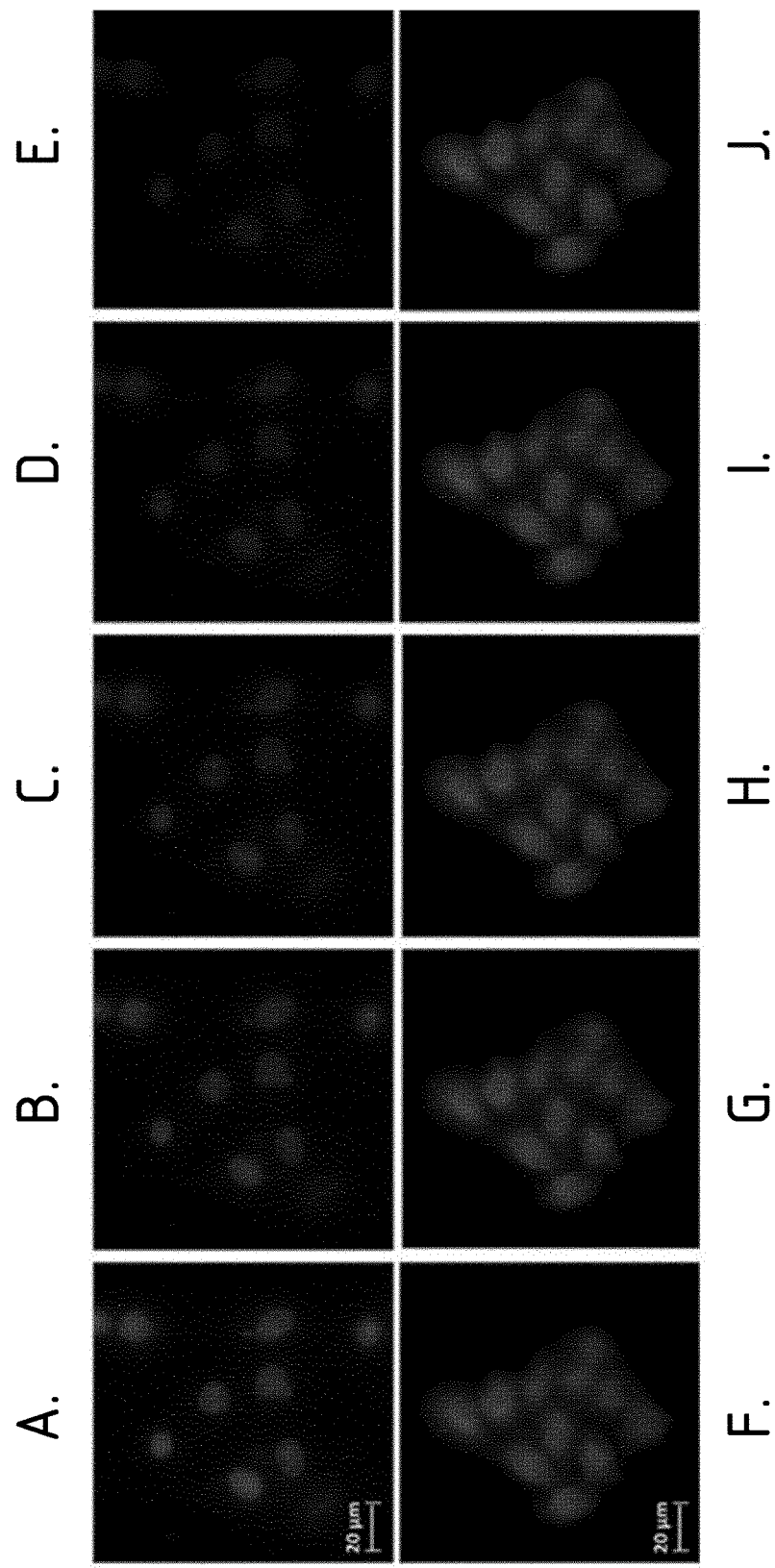
FIG. 8. (A)-(J) illustrate results of photobleaching experiments obtained by epifluorescence microscopy in necrotic HeLa cells incubated with 45 µM $Yb^{3+}[Zn(II)MC_{pyzHA}]$ for 15 min or 3 µM PI for 5 min. (Top) PI, visible emission ($\lambda_{ex}$=550 nm, band pass filter with 25 nm bandwidth; $\lambda_{em}$=605 nm, band pass filter with 70 nm bandwidth; exposure time: 100 ms) after a continuous excitation with a 550 nm band pass filter (25 nm bandwidth) during: (A) 10 s, (B) 50 s, (C) 100 s, (D) 200 s, (E) 500 s. (Bottom) $Yb^{3+}[Zn(II) MC_{pyzHA}]$, NIR emission arising from $Yb^{3+}$ ($\lambda_{ex}$=447 nm, band pass filter with 60 nm bandwidth; $\lambda_{em}$=805 nm, long-pass filter; exposure time: 10 s) after continuous excitation with a 447 nm band pass filter (60 nm bandwidth) during: (F) 10 s, (G) 50 s, (H) 100 s, (I) 200 s, (J) 500 s. 63× objective.

The results shown in Fig. (A)-(E) are for the cells with the short incubation and no UV light exposure. In addition to the results in FIG. 18, (A)-(E), the results in FIG. 7, (A)-(E) demonstrate that the metallacrowns (e.g., $Yb^{3+}[Zn(II)MC_{pyzHA}]$) are going exclusively in necrotic cells. The NIR staining of the nucleus and cytoplasm was also evident from these results.

Figure 22:
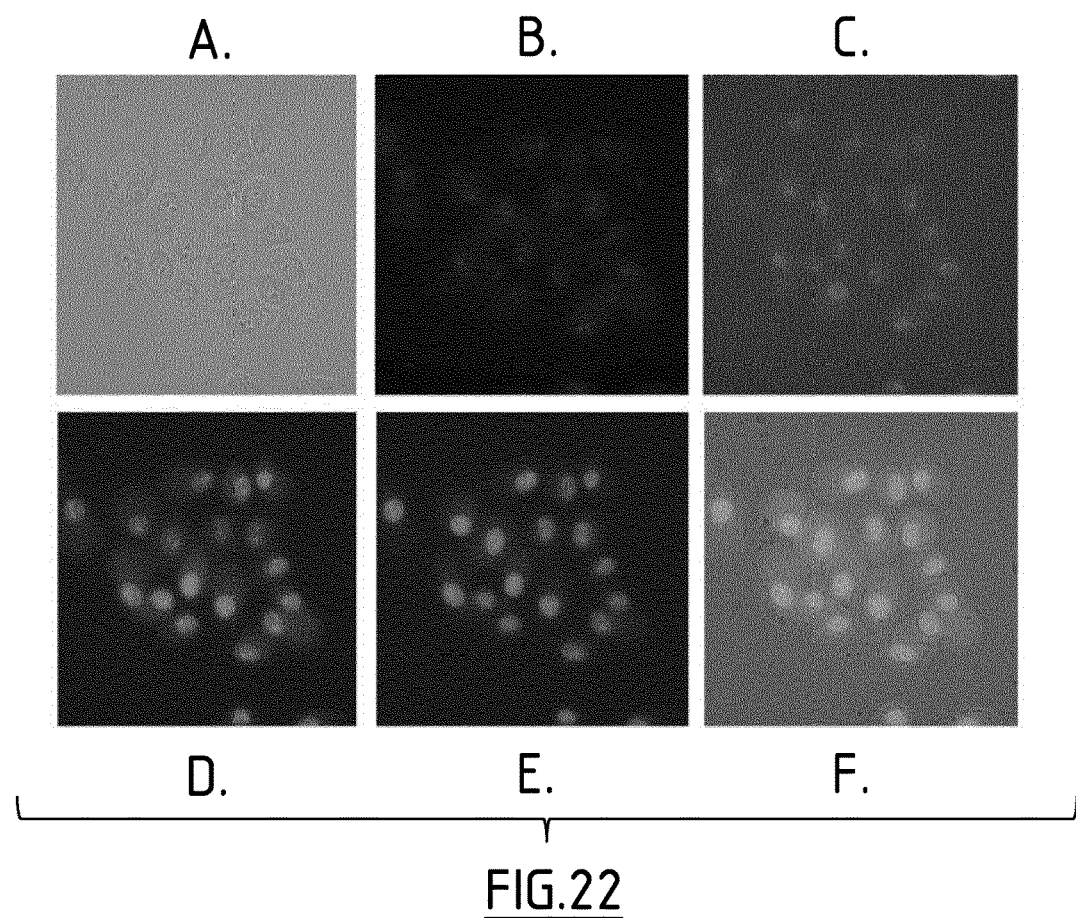
FIG. 22. (A) through (F) are images (40× magnification), obtained using NIR epifluorescence microscopy, of HeLa cells incubated with 150 μM of $Yb^{3+}[Zn(II)MC_{pyzHA}]$ and with 3 μM propidium iodide for 15 minutes, illuminated with UV light (377 nm) for 5 minutes, further incubated for 1 hour. (A) is the brightfield image; (B) is the visible signal arising from propidium iodide obtained after 80 ms of exposure time ($\lambda_{em}$=605 nm 70 nm band pass filter and $\lambda_{ex}$=550 nm with 25 nm band pass filter); (C), (D), and (E) show the visible signals arising from propidium iodide and the emission signal arising from $Yb^{3+}[Zn(II)MC_{pyzHA}]$ in the NIR range ($\lambda_{em}$=805 nm long pass filter) obtained after 8 s of exposure to excitation ($\lambda_{ex}$=447 nm band pass filter with 60 nm bandwidth) after 5, 10, 15 and 20 minutes of incubation, respectively (in (E), emission from PI and emission from $Yb^{3+}[Zn(II)MC_{pyzHA}]$ were observed after 20 minutes); and (F) is (A) and (E) merged together.

The results shown in FIG. 22, (A)-(F) are for the cells with the short incubation and UV light exposure #2. These results also confirmed that $Yb^{3+}[Zn(II)MC_{pyzHA}]$ is going in necrotic cells. After incubation of HeLa cells with $Yb^{3+}[Zn(II)MC_{pyzHA}]$ and propidium iodide for 20 minutes, cells were illuminated with UV light for 5 minutes in order to damage cell membrane and induce cell death (necrosis and/or apoptosis). After 15 min of incubation, emission from propidium iodide was observed in the visible range, and after 5 more minutes, emission in NIR from $Yb^{3+}[Zn(II)MC_{pyzHA}]$ was observed. From this experiment, it can be concluded that both dyes are specific for dead and apoptotic cells with different kinetics.

Figure 23:
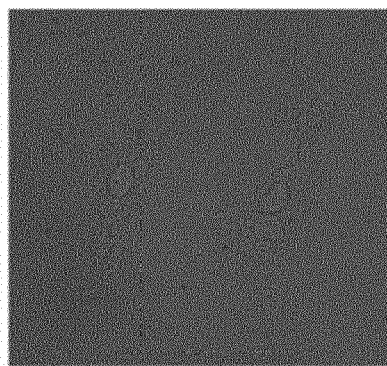
FIG. 23. (A) through (C) are images (40× magnification), obtained using NIR epifluorescence microscopy, of Mesenchymal Stem Cells (MSC) incubated with 150 μM of $Yb^{3+}[Zn(II)MC_{pyzHA}]$ for 15 minutes, illuminated with UV light (377 nm) for 5 minutes, further incubated for 1 hour, and washed with OPTI-MEM® media for 5 minutes. (A) is the brightfield image; (B) shows the emission signal arising from $Yb^{3+}[Zn(II)MC_{pyzHA}]$ in the NIR range ($\lambda_{em}$=805 nm long pass filter) obtained after 8 s of exposure to excitation ($\lambda_{ex}$=447 nm band pass filter with 60 nm bandwidth); and (C) is (A) and (B) merged.
Figure 23:
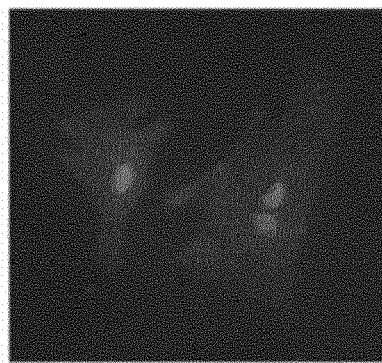
Figure 23:
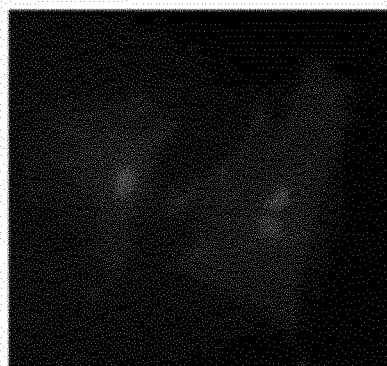

The results shown in FIG. 23, (A)-(C) are for the cells with the short incubation and UV light exposure #3. The same photochemical effect seen with the HeLa cell line occurred with the MSC cells. In the case of MSC cells, the Yb$^{3+}$[Zn(II)MC$_{pyzHA}$] is also acting as an NIR dye and cell fixative.

Example 2—NIR Epifluorescent Microscopy of the Yb$^{3+}$[Zn(II)MC$_{pyzHA}$] Complex with HeLa Cancer Cells Treated with N-Acetyl Cysteine Formation of extracellular vesicles is a result of cellular response on oxidative stress which indicates excessive production of ROS (Reactive oxygen species). In order to investigate if ROS are responsible for dual function of Yb$^{3+}$[Zn(II)MC$_{pyzHA}$], HeLa cancer cells were treated with NAC (N-acetyl cysteine), which is a well known antioxidant that efficiently blocks production of reactive oxygen species (ROS).

Experimental Conditions

HeLa (Human Epithelial Ovarian Carcinoma) cell line obtained from ATCC (Molsheim, France) was cultured in Dulbecco's modified Eagle's medium (DMEM) supplemented with 10% heat-inactivated fetal bovine serum (FBS), 1% of 100× non-essential aminoacid solution, 1% of L-glutamine (GlutaMAX) and 1% of streptomycin/penicillin antibiotics. Cells were seeded in a 8-well Lab Tek Chamber coverglass (Nunc, Dutsher S.A., Brumath, France) at a density of 6×10$^4$ cells/well and cultured at 37° C. in 5% humidified CO$_2$ atmosphere.

NAC Incubation First:

After 24 hours, the cell culture media was removed. Some of the cells were washed twice with OPTI-MEM® media (room temperature), incubated with N-acetyl cysteine (NAC) for 15 minutes, washed twice with OPTI-MEM® media and incubated with 150 μM of Yb$^{3+}$[Zn(II)MC$_{pyzHA}$] for 15 minutes.

Yb$^{3+}$[Zn(II)MC$_{pyzHA}$] Incubation First:

After 24 hours, the cell culture media was removed. Some of the cells were washed twice with OPTI-MEM® media (room temperature), and incubated with 150 μM of Yb$^{3+}$[Zn(II)MC$_{pyzHA}$] for 15 minutes. N-acetyl cysteine (NAC) was added, and the cells were incubated for another 30 minutes. The cells were washed twice with OPTI-MEM® media.

Prior to epifluorescent imaging, the cells were washed trice with OPTI-MEM® (room temperature) in order to remove any non-specifically bound Yb$^{3+}$[Zn(II)MC$_{pyzHA}$] complex. The cells were observed with a Zeiss Axio Observer Z1 fluorescence inverted microscope (Zeiss, Le Pecq, France) equipped with an EMCCD Evolve 512 (Roper Scientific) photometric camera or ORCA-R2 high resolution CCD camera. The light source, Zeiss HXP 120, was combined with the following filter cubes: 377 nm band pass 50 nm filter for the excitation and long pass filter 805 nm or 996 nm band pass filter 70 nm for Yb$^{III}$ emission in the NW range.

Experimental Results

Figure 25:
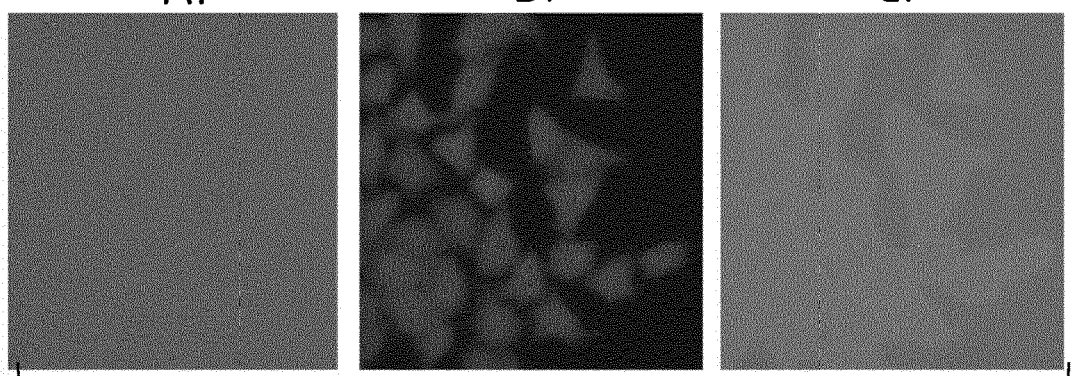
FIG. 25. (A) through (C) are images (40× magnification), obtained using NIR epifluorescence microscopy, of HeLa cells incubated with N-acetyl cysteine (NAC) for 15 minutes, washed with OPTI-MEM® media, and incubated with 150 μM $Yb^{3+}[Zn(II)MC_{pyzHA}]$ for 15 minutes. (A) is the brightfield image; (B) is the emission signal image arising from $Yb^{3+}[Zn(II)MC_{pyzHA}]$ in the NIR range ($\lambda_{em}$=805 nm long pass filter) obtained after 400 ms of exposure to excitation ($\lambda_{ex}$=377 nm band pass filter with 40 nm bandwidth); and (C) is (A) and (B) merged together.

The results from the NAC Incubation First experiment are shown in FIGS. 25, (A) through (C). FIG. 25, (B) shows a very good signal in NIR with very short exposure time (400 ms), which indicates that modulation of metabolism through signal transduction pathways in cancer cells has an influence on the efficiency of Yb$^{3+}$[Zn(II)MC$_{pyzHA}$] complex as an NIR dye, as well as on their internalization in the cells. From these results, it can be concluded that production of ROS is not responsible for dual function of Yb$^{3+}$[Zn(II)MC$_{pyzHA}$] complex.

Figure 26:
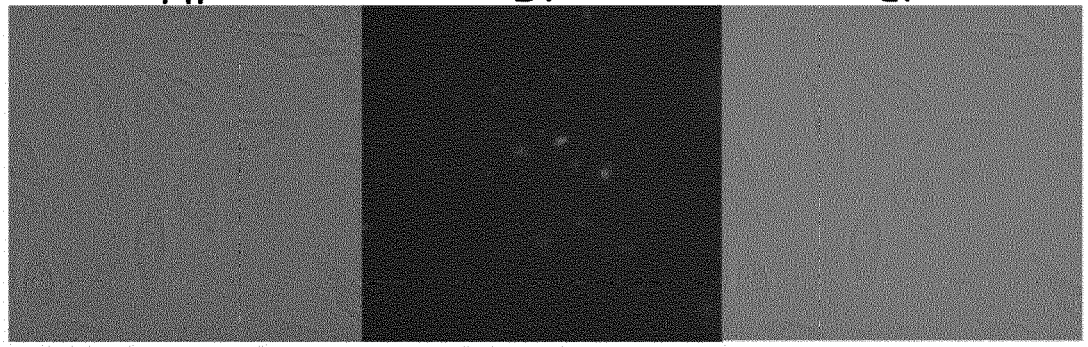
FIG. 26. (A) through (C) are images (40× magnification), obtained using NIR epifluorescence microscopy, of HeLa cells incubated with 150 μM $Yb^{3+}[Zn(II)MC_{pyzHA}]$ for 15 minutes, and then incubated with N-acetyl cysteine (NAC) for 30 minutes. (A) is the brightfield image; (B) is the emission signal image arising from $Yb^{3+}[Zn(II)MC_{pyzHA}]$ in the NIR range ($\lambda_{em}$=805 nm long pass filter) obtained after 5 s of exposure to excitation ($\lambda_{ex}$=377 nm band pass filter with 40 nm bandwidth); and (C) is (A) and (B) merged together.
Figure 27:
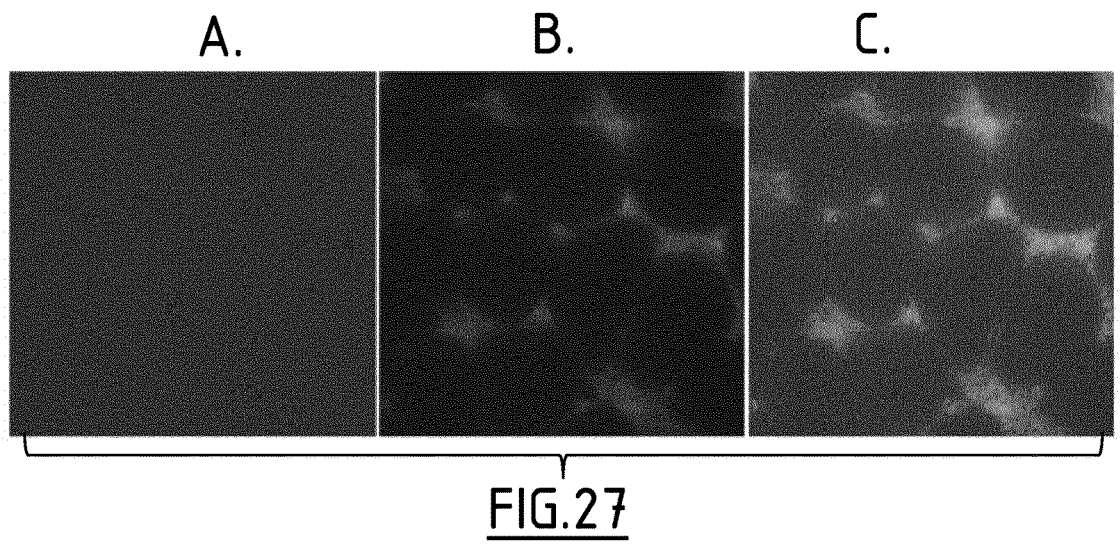
FIG. 27. (A) through (C) are images (63× magnification), obtained using NIR epifluorescence microscopy, of HeLa cells incubated with 200 μM $Nd^{3+}[Zn(II)MC_{(pyzHA)x(quinoHA)y}]$ for 3 hours, and washed with OPTI-MEM® media. (A) is the brightfield image; (B) is the emission signal image arising from $Nd^{3+}[Zn(II)MC_{(pyzHA)x(quinoHA)y}]$ in the NIR range ($\lambda_{em}$=805 nm long pass filter) obtained after 20 s of exposure to excitation ($\lambda_{ex}$=536 nm band pass filter with 40 nm bandwidth); and (C) is (A) and (B) merged.
Figure 28:
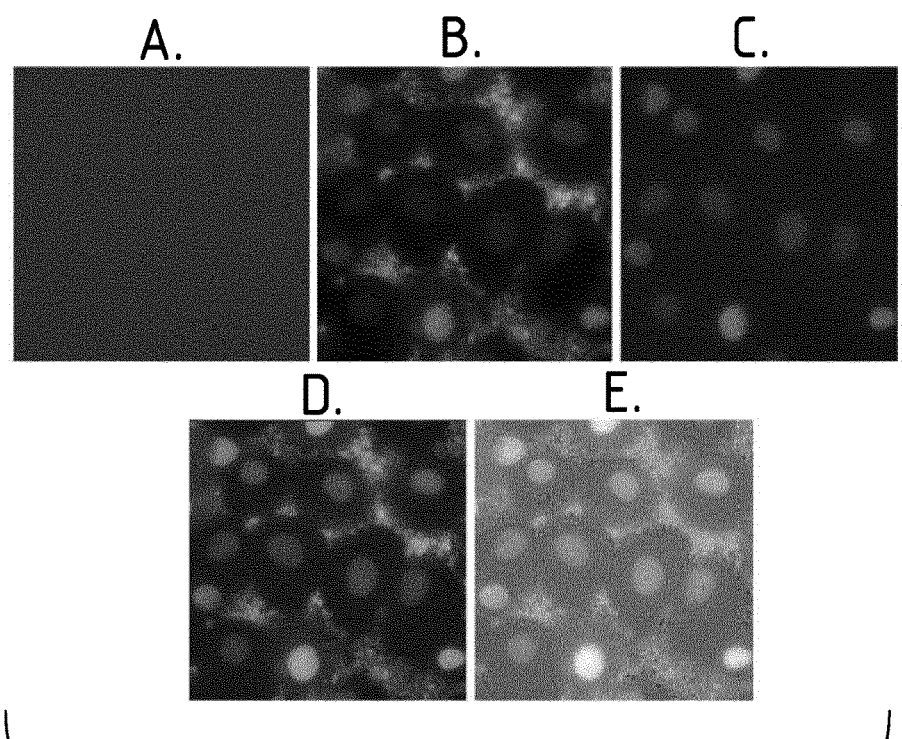
FIG. 28. (A) through (E) are images (40× magnification), obtained using NIR epifluorescence microscopy, of HeLa cells incubated with 200 μM $Nd^{3+}[Zn(II)MC_{(pyzHA)x(quinoHA)y}]$ for 3 hours, washed with OPTI-MEM® media, illuminated with UV light (377 nm) for 10 minutes, further incubated for 1.5 hours, and incubated with 3 μM propidium iodide for 5 minutes. (A) is the brightfield image; (B) shows the emission signal arising from $Nd^{3+}[Zn(II)MC_{(pyzHA)x(quinoHA)y}]$ in the NIR range ($\lambda_{em}$=805 nm long pass filter) obtained after 20 s of exposure to excitation ($\lambda_{ex}$=536 nm band pass filter with 40 nm bandwidth); (C) shows the visible signal arising from propidium iodide obtained after 80 ms of exposure time ($\lambda_{em}$=617 nm band pass filter and $\lambda_{ex}$=535 nm band pass filter with 40 nm bandwidth); (D) is (B) and (C) merged; and (E) is (A), (B) and (C) merged.
Figure 29:
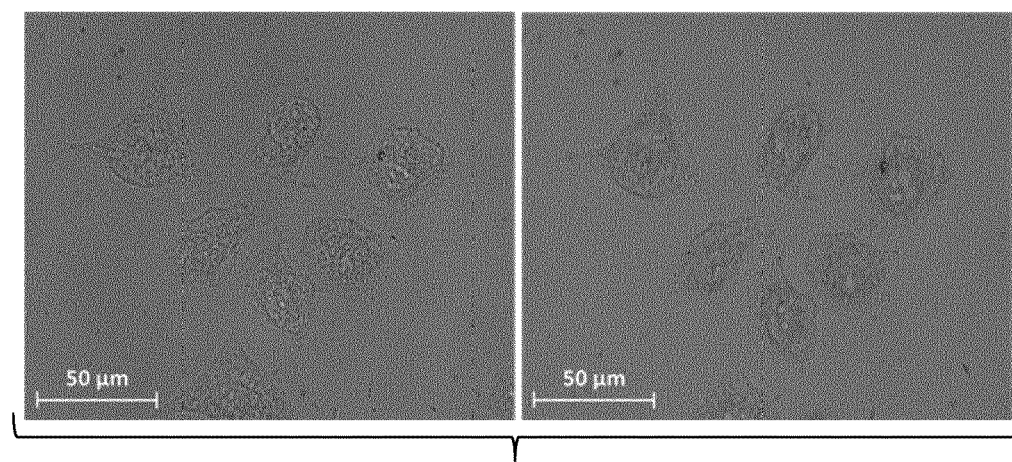
FIGS. 29. (A) and (B) illustrate the images of HeLa cells fixed with $Yb^{3+}[Zn(II)MC_{pyzHA}]$ obtained under epifluorescence microscopy. Brightfield images of fixed cells were recorded after different incubation time at 37° C. in Opti-MEM: (A) 1 h and (B) 1 month.

The results from the Yb$^{3+}$[Zn(II)MC$_{pyzHA}$] Incubation First experiment are shown in FIG. 26, (A) through (C). FIG. 26, (B) shows the NIR signal of Yb$^{3+}$[Zn(II)MC$_{pyzHA}$] just in the cell culture media, outside of the cells. These results do not show internalization of the MC complexes inside of the cells. These results indicate that if the metabolism of the cells is not modified (in the specific way that it is stopping production of ROS species), there will not be internalization of Yb$^{3+}$[Zn(II)MC$_{pyzHA}$] in the cells. These results confirm the results of the previous experiment (NAC Incubation First) where it was shown that modulation of metabolism through signal transduction pathways in cancer cells has an influence on the efficiency of Yb$^{3+}$[Zn(II)MC$_{pyzHA}$] (also described as YbZn$_{16}$(pyz)$_{16}$MC) complex as an NIR dye, as well as on their internalization in the cells.

Example 3—Confocal Microscopy of the Yb$^{3+}$[Zn(H)MC$_{pyzHA}$] Complex with HeLa Cancer Cells or Mesenchymal Stem Cells (MSC)

Experimental Conditions

For these confocal microscopy experiments, the HeLa or MSC cells were prepared in the same way as for the epifluorescence microscopy experiments (see Example 1, Short incubation, UV light exposure #1 and #3). The cells were observed with a confocal laser scanning microscopy (CLSM) on a Zeiss Axiovert 200M microscope equipped with LSM 510 Meta scanning device (Zeiss, France). Complexes were excited with Argon laser at 458 nm and emission signal was collected from 499 nm to 799 nm. During this experiment, a 63× Plan-Apochromat objective was used (2× zoom).

Experimental Results

Figure 19:
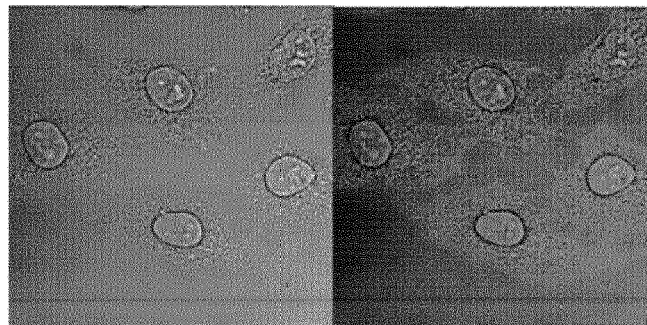
FIG. 19. (A) through (C) are confocal microscopy images (63× magnification, 2× zoom) of HeLa cells incubated with 150 μM Yb$^{3+}$[Zn(II)MC$_{pyzHA}$] for 15 minutes, illuminated with UV light (377 nm) for 8 minutes, followed by further incubation for 1 hour ($\lambda_{ex}$=458 nm, $\lambda_{em}$=499-799 nm). (A) is the brightfield image; (B) shows the visible signal arising from Yb$^{3+}$[Zn(II)MC$_{pyzHA}$]; and (C) is (A) and (B) merged together.
Figure 24:
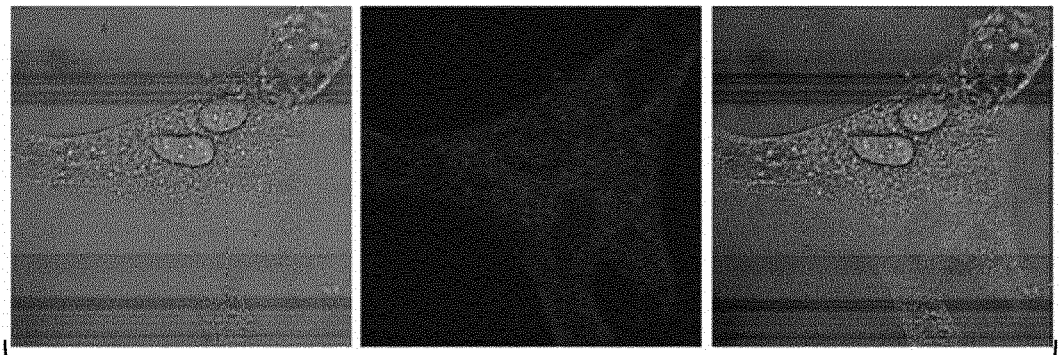
FIG. 24. (A) through (C) are confocal microscopy images (63× magnification, 2× zoom) images of MSC (Mesenchymal Stem Cells) incubated with 150 μM $Yb^{3+}[Zn(II)MC_{pyzHA}]$ for 15 minutes, illuminated with UV light (377 nm) for 8 minutes, followed by further incubation for 1 hour ($\lambda_{ex}$=458 nm, $\lambda_{em}$=499-799 nm). (A) is the brightfield image; (B) is the visible signal arising from $Yb^{3+}[Zn(II)MC_{pyzHA}]$; and (C) is (A) and (B) merged together.

FIGS. 19A-19C are the confocal images for the HeLa cells and FIG. 24, (A)-(C) are the confocal images for the MSC stem cells. In FIG. 19, (B) and FIG. 24, (B), emission was observed from Yb$^{3+}$[Zn(II)MC$_{pyzHA}$], arising from the ligands, in the visible range. This emission enabled the use of confocal microscopy. This experiment confirmed that Yb$^{3+}$[Zn(II)MC$_{pyzHA}$] (and other Ln$^{3+}$Zn(II)MC$_{pyzHA}$D are specifically located in nucleus as well as in cytoplasm of HeLa cancer cells and of MSC stem cells.

Example 4—Cytotoxicity Assay

In order to determine if the LnZn$_{16}$(pyz)$_{16}$MC complexes (Ln$^{3+}$Zn(II)MC$_{HA}$D are toxic for live cells, cytotoxicity tests with Alamar blue were performed.

Alamar blue is viability reagent which functions as a cell health indicator by using the reducing power of living cells to quantitatively measure the proliferation of different human and animal cell lines. This enables the cytotoxicity of different chemical complexes to be determined. The active ingredient of Alamar Blue is resazurin, which is non-toxic and cell permeable compound, and upon entering in the cells, it is reduced to highly fluorescent resorufin.

Experimental Conditions

The cytotoxicity tests were performed with Alamar blue assay (Invitrogen, France). HeLa cells were seeded in 96-well plate at the density of 1*10$^4$ cells per well and cultured at 37° C. in 5% humidified CO$_2$ atmosphere. After 24 hours of attachment, the cells were incubated with different concentrations of Yb$^{3+}$[Zn(II)MC$_{pyzHA}$] in cell culture medium for 24 and 48 hours followed by incubation with Alamar blue (10% v/v) for 3 to 4 hours at 37° C. in 5% humidified CO$_2$ atmosphere.

Fluorescence of Alamar blue was measured with plate reader (Victor 3V, Perkin Elmer, France), with excitation at 530 nm and emission at 590 nm, for cells incubated with $Yb^{3+}[Zn(II)MC_{pyzHA}]$ and for untreated cells (control).

Experimental Results

Figure 6:
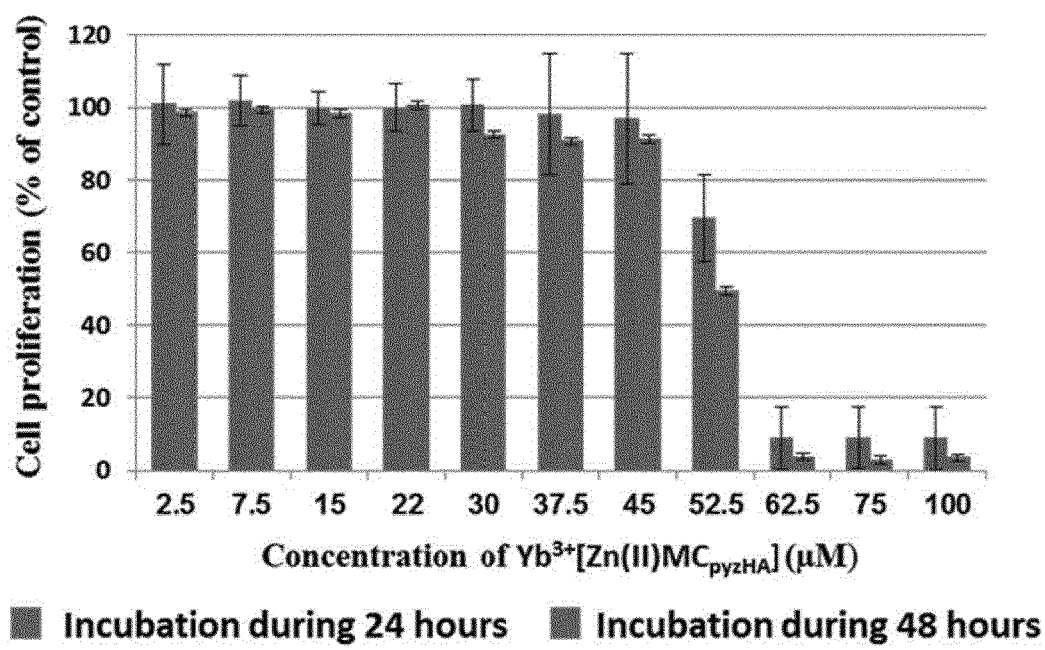
FIG. 6 is a graph depicting the results of a cytotoxicity test of HeLa cells incubated in with $Yb^{3+}[Zn(II)MC_{pyzHA}]$ for 24 an 48 hours, and then in Alamar blue.
Figure 13:
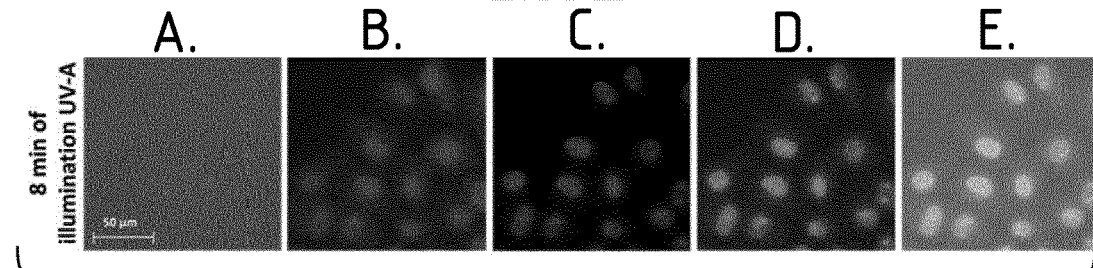
FIG. 13. (A) to (E) illustrate results of epifluorescence microscopy experiments on HeLa cells fixed with 150 μM Yb$^{3+}$[Zn(II)MC$_{pyzHA}$] and illumination with the UV-A light obtained through a 377 nm band pass filter (50 nm bandwidth) for 8 min. After fixation, the cells were washed and incubated with 3 μM PI for 5 min. (A) Brightfield. (B) NIR signal arising from Yb$^{3+}$[Zn(II)MC$_{pyzHA}$] ($\lambda_{ex}$: 447 nm band pass filter with 60 nm bandwidth, $\lambda_{em}$: 805 nm longpass filter, exposure time: 8 s). (C) Visible signal arising from PI ($\lambda_{ex}$: 550 nm band pass filter with 25 nm bandwidth, $\lambda_{em}$: 605 nm band pass filter with 70 nm bandwidth, exposure time: 800 ms). (D) Merged image obtained by the combination of the PI and Yb$^{3+}$[Zn(II)MC$_{pyzHA}$] images. (E) Merged image obtained by the combination of the PI, Yb$^{3+}$[Zn(II)MC$_{pyzHA}$] and brightfield images. 63× objective.
Figure 14:
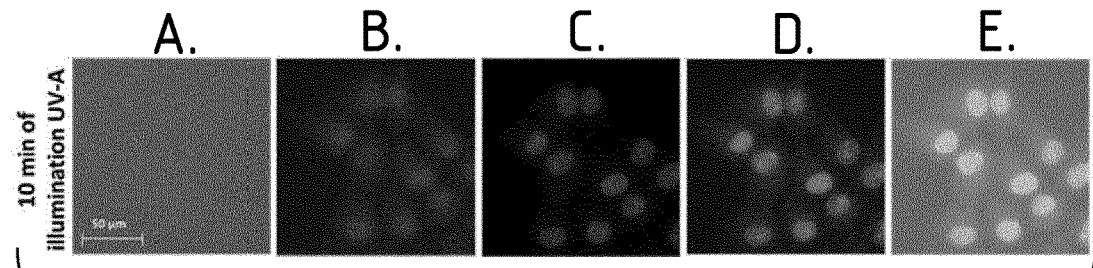
FIG. 14. (A) to (E) illustrate results of epifluorescence microscopy experiments on HeLa cells fixed with 150 μM Yb$^{3+}$[Zn(II)MC$_{pyzHA}$] and illumination with the UV-A light obtained through a 377 nm band pass filter (50 nm bandwidth) during 10 min. After fixation, the cells were washed and incubated with 3 μM PI for 5 min. (A) Brightfield. (B) NIR signal arising from Yb$^{3+}$[Zn(II)MC$_{pyzHA}$] ($\lambda_{ex}$: 447 nm band pass filter with 60 nm bandwidth, $\lambda_{em}$: 805 nm longpass filter, exposure time: 8 s). (C) Visible signal arising from PI ($\lambda_{ex}$: 550 nm band pass filter with 25 nm bandwidth, $\lambda_{em}$: 605 nm band pass filter with 70 nm bandwidth, exposure time: 800 ms). (D) Merged image obtained by the combination of the PI and Yb$^{3+}$[Zn(II)MC$_{pyzHA}$] images. (E) Merged images obtained by the combination of the PI, Yb$^{3+}$[Zn(II)MC$_{pyzHA}$] and brightfield images. 63× objective.
Figure 15:
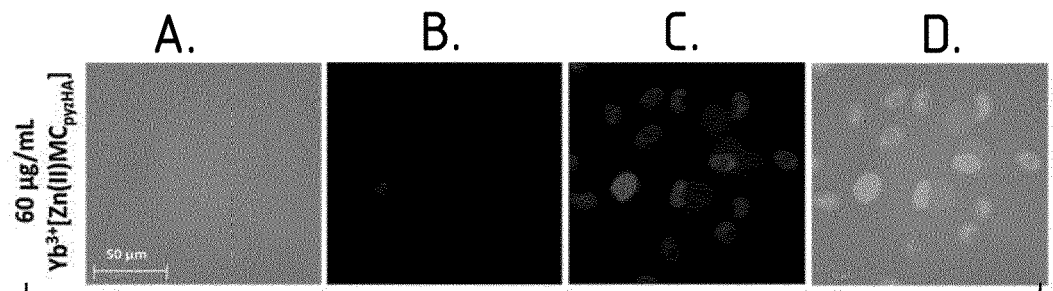
FIG. 15. (A) to (D) illustrate results of the epifluorescence microscopy experiments on HeLa cells fixed with 15 μM concentration of Yb$^{3+}$[Zn(II)MC$_{pyzHA}$] and illumination with the UV-A light during 8 min followed by the washing with Opti-MEM cell culture medium and by the incubation with 3 μM PI during 5 min. (A) Brightfield. (B) NIR signal arising from Yb$^{3+}$[Zn(II)MC$_{pyzHA}$] ($\lambda_{ex}$: 447 nm band pass filter with 60 nm bandwidth, $\lambda_{em}$: 805 nm longpass filter, exposure time: 8 s). (C) Visible signal arising from PI ($\lambda_{ex}$: 550 nm band pass filter with 25 nm bandwidth, $\lambda_{em}$: 605 nm band pass filter with 70 nm bandwidth, exposure time: 800 ms). (D) Merged image obtained by the combination of the PI, Yb$^{3+}$[Zn(II)MC$_{pyzHA}$] and brightfield images. 63× objective.

The cytotoxicity test results for the cells exposed to different concentrations of $Yb^{3+}[Zn(II)MC_{pyzHA}]$ for 24 and 48 hours are shown in FIG. 13, and the cytotoxicity test results for the cells exposed to different concentrations of $Yb^{3+}[Zn(II)MC_{pyzHA}]$ for 5 hours are shown in FIG. 6. As illustrated in FIG. 6, $Yb^{3+}[Zn(II)MC_{pyzHA}]$ started to be significantly toxic from 45 µM concentration, where approximately 70% of cells remained alive.

Example 5—NIR Epifluorescent Microscopy of the $Nd^{3+}[Zn(II)MC_{pyzHA}]$ Complex with HeLa Cancer Cells Experimental Conditions HeLa cells were cultured and seeded as previously described in Example 1. In this example, $Nd^{3+}[Zn(II)MC_{pyzHA}]$ complexes were used. The HeLa cells were washed twice with OPTI-MEM® media (room temperature), incubated with a solution of 150 µM $Nd^{3+}[Zn(II)MC_{pyzHA}]$ complex in OPTI-MEM® media (supplemented with 2% of FBS at 37° C. in 5% $CO_2$ atmosphere) for 15 minutes, illuminated with UV light (377 nm) for 8 minutes, and then were allowed to continue incubating for 1 hour. The continued incubation enabled the internalization of the complex.

Prior to epifluorescent imaging, the HeLa cells were washed trice with OPTI-MEM® (room temperature) in order to remove any non-specifically bound $Nd^{3+}[Zn(II)MC_{pyzHA}]$ complex. The cells were observed with a Zeiss Axio Observer Z1 fluorescence inverted microscope (Zeiss, Le Pecq, France) equipped with an EMCCD Evolve 512 (Roper Scientific) photometric camera or ORCA-R2 high resolution CCD camera. The light source, Zeiss HXP 120, was combined with the following filter cubes: 377 nm with 50 nm band pass filter for the excitation and long pass filter 805 nm for $Nd^{3+}$ emission in the NIR range.

Experimental Results

The epifluorescent imaging results are shown in FIG. 24, (A)-(C). The HeLa cells were fixed and stained with the $Nd^{3+}[Zn(II)MC_{pyzHA}]$ complex, just as they were for the $Yb^{3+}[Zn(II)MC_{pyzHA}]$ complex.

Example 6—NIR Epifluorescent Microscopy of the $Nd^{3+}[Zn(II)MC_{(pyzHA)x(quinoHA)y}]$ Complex with HeLa Cancer Cells Experimental Conditions HeLa cells were cultured in the same manner as described in Example 5. After 24 hours of cell culturing in a 8-well Lab Tek Chamber coverglass (Nunc, Dutsher S.A., Brumath, France), cell culture media was removed, cells were washed twice with OPTI-MEM® media (room temperature).

The cells were incubated with a solution of 200 µM $Nd^{3+}[Zn(II)MC_{(pyzHA)x(quinoHA)y}]$ (or $NdZn_{16}(pyz)_x(quino)_y$ MC) complex in OPTI-MEM® media (supplemented with 2% of FBS at 37° C. in 5% $CO_2$ atmosphere) for 3 hours. In order to induce cell apoptosis and to allow internalization of the $Nd^{3+}[Zn(II)MC_{(pyzHA)x(quinoHA)y}]$ complex inside of the nucleus, the incubating cells were illuminated with UV-A light for 10 minutes, followed by continued incubation for another 1.5 hours. Some of the cells were also then incubated with 3 µM propidium iodide for 5 minutes.

Prior to epifluorescent imaging, the cells were washed trice with OPTI-MEM® media (room temperature) in order to remove any non-specifically bound $Nd^{3+}[Zn(II)MC_{(pyzHA)x(quinoHA)y}]$ complex. The cells were observed with a Zeiss Axio Observer Z1 fluorescence inverted microscope (Zeiss, Le Pecq, France) equipped with an EMCCD Evolve 512 (Roper Scientific) photometric camera or ORCA-R2 high resolution CCD camera. The light source, Zeiss HXP 120, was combined with the following filter cubes:

a. 377 nm with 50 nm band pass filter for the excitation and long pass filter 805 nm or 895 nm with 90 nm band pass filter for $Nd^{III}$ emission in the NIR range.

b. 536 nm with 40 nm band pass for the excitation and long pass filter 805 nm or 895 nm with 90 nm band pass filter for $Nd^{III}$ emission in the NIR range.

c. 480 nm with 50 nm band pass for the excitation and long pass filter 805 nm or 895 nm with 90 nm band pass filter for $Nd^{III}$ emission in the NIR range.

Experimental Results

Figure 16:
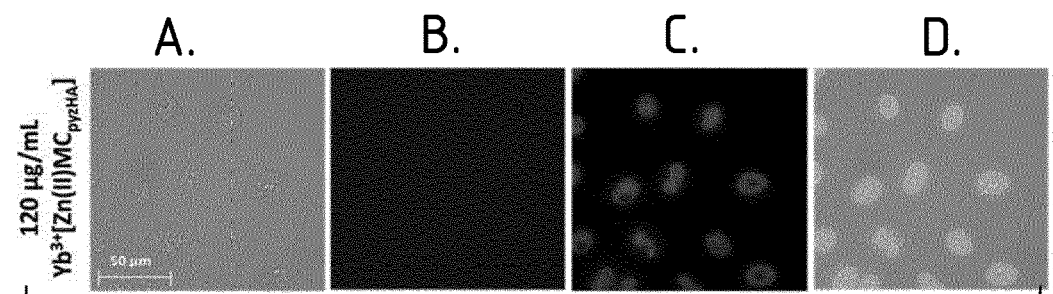
FIG. 16 illustrates results of the epifluorescence microscopy experiments on HeLa cells fixed with 30 μM concentration of Yb$^{3+}$[Zn(II)MC$_{pyzHA}$] and illumination with the UV-A light during 8 min followed by the washing with Opti-MEM cell culture medium and by the incubation with 3 μM PI during 5 min. (A) Brightfield. (B) NIR signal arising from Yb$^{3+}$[Zn(II)MC$_{pyzHA}$] $\lambda_{ex}$: 447 nm band pass filter with 60 nm bandwidth, $\lambda_{em}$: 805 nm long pass filter, exposure time: 8 s). (C) Visible signal arising from PI ($\lambda_{ex}$: 550 nm band pass filter with 25 nm bandwidth, $\lambda_{em}$: 605 nm band pass filter with 70 nm bandwidth, exposure time: 800 ms). (D) Merged image obtained by the combination of the PI, Yb$^{3+}$[Zn(II)MC$_{pyzHA}$] and brightfield images. 63× objective.

The results for the cells without UV exposure are shown in FIG. 16, (A)-(C). MCs formed with two different ligands, PyzHA and QuinoHA, exhibit specific properties in biological conditions. These MCs serve as a NIR dye for the cell membrane (as evidenced in FIG. 16, (B)).

Moreover, with this composition of MCs, the excitation wavelength shifted toward lower energy, where these complexes can be excited up to 536 nm. This shift in excitation energy is important because it allow penetration through the tissue as well as better detection sensitivity because of lower absorption of the biological molecules (lipids, proteins, hemoglobin, etc.) for these wavelengths.

Figure 17:
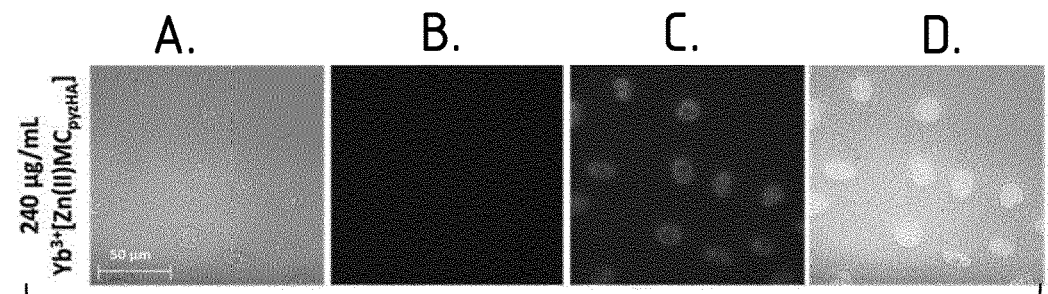
FIG. 17 illustrates results of the epifluorescence microscopy experiments on HeLa cells fixed with 60 μM concentration of Yb$^{3+}$[Zn(II)MC$_{pyzHA}$] and illumination with the UV-A light during 8 min followed by washing with Opti-MEM cell culture medium and incubation with 3 μM PI during 5 min. (A) Brightfield. (B) NIR signal arising from Yb$^{3+}$[Zn(II)MC$_{pyzHA}$] ($\lambda_{ex}$: 447 nm band pass filter with 60 nm bandwidth, $\lambda_{em}$: 805 nm longpass filter, exposure time: 8 s). (C) Visible signal arising from PI ($\lambda_{ex}$: 550 nm band pass filter with 25 nm band width, $\lambda_{em}$: 605 nm band pass filter with 70 nm bandwidth, exposure time: 800 ms). (D) Merged image obtained by the combination of PI, Yb$^{3+}$[Zn(II)MC$_{pyzHA}$] and brightfield images. 63× objective.

The results for the cells with UV exposure are shown in FIGS. 17, (A)-(E). The exposure of HeLa cells to UV-A light (377 nm) for 10 minutes damaged the cell membrane and induced apoptosis (programmed cell death) and/or necrosis (unprogrammed cell death) of the cells. This allowed for internalization of the $Nd^3[Zn(II)MC_{(pyzHA)x(quinoHA)y}]$ complex in the nucleus (as illustrated in FIG. 17, (B)). This experiment also indicates that the same photochemical effect (as seen with $Yb^{3+}[Zn(II)MC_{pyzHA}]$) takes place.

Example 7—Photostability/Photophysical Properties

Photostability Stress Tests

Photostability stress tests of $Yb^{3+}[Zn(II)MC_{pyzHA}]$ (Yb $\lambda_{em}=980$ nm) and $Nd^{3+}[Zn(II)MC_{pyzHA}]$ (Nd $\lambda_{em}=1064$ nm) and the commercially available dye for necrotic cells (Propidium Iodide) were performed. The complexes (150 µM) or dye (50 µM) were dissolved in water and the complexes were also dissolved in OPTI-MEM® media. The MC solutions were exposed to 5 hours of UV radiation (377 nm). The propidium iodide solution was exposed to 5 hours of UV radiation (530 nm). The results are shown in FIGS. 18, (A) and (B). The results show that both MC complexes were fully photostable during 5 hours of irradiation with 377 nm light, while the fluorescence intensity of the propidium iodide dropped half of its initial intensity upon irradiation at 530 nm.

Figure 20:
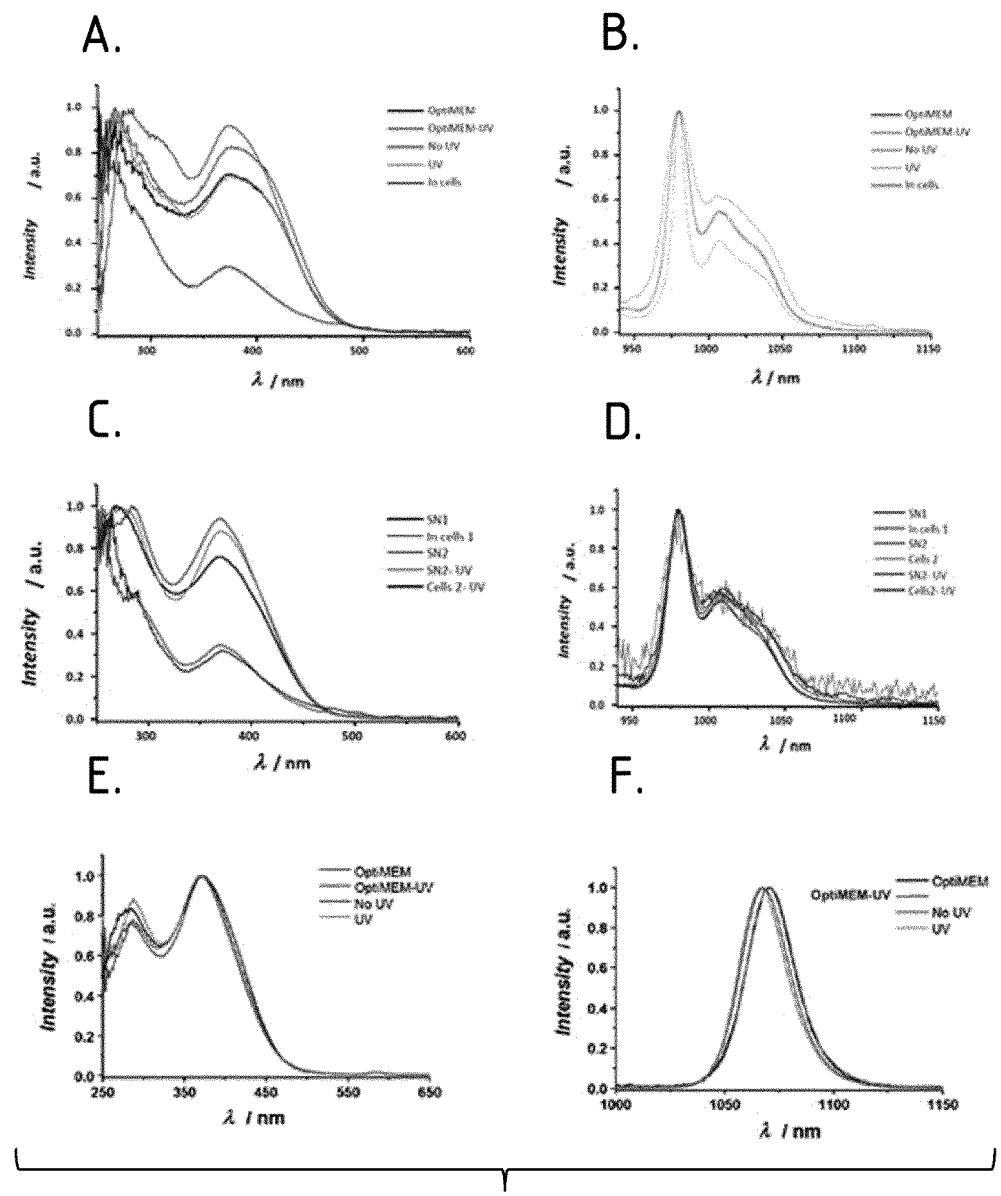
FIGS. 20. (A) and (B) are graphs illustrating the corrected and normalized excitation ($\lambda_{em}$=980 nm) and emission spectra ($\lambda_{ex}$=370 nm), respectively, of Yb$^{3+}$[Zn(II)MC$_{pyzHA}$] complexes in OPTI-MEM® media and in HeLa cells, both with and without UV exposure.

Photophysical Properties of $Yb^{3+}[Zn(II)MC_{pyzHA}]$ in the HeLa Cancer Cells The $Yb^{3+}[Zn(II)MC_{pyzHA}]$ complexes were dissolved in OPTI-MEM® medium with 2% SVF (without cells) and were incorporated in HeLa cells, both with and without exposure to UV light. The results in are shown in FIG. 20, (A) (corrected and normalized excitation) and FIG. 20, (B) (corrected and normalized emission). These experiments showed that the spectroscopic properties of MCs ($Yb^{3+}[Zn(II)MC_{pyzHA}]$) can be controlled in cell culture media and in HeLa cancer cells under different experimental conditions.

The present inventors developed instrumentation in order to collect photophysical properties of MCs inside of cancer cells. They measured quantitative photophysical parameters (quantum yields and life times) inside of the cells with equipment which is usually adapted for measuring of (quantum yields and life times) in solids or in concentrated solutions. The results showed that luminescent properties of the MC complexes did not change in the cells, as an indication that their structures remain intact.

The $Yb^{3+}[Zn(II)MC_{pyzHA}]$ complexes were collected together with cell supernatant (SN) and with HeLa cells treated with N-acetyl cysteine, both with and without exposure to UV light. For SN1 and cells1, incubation with NAC took place for 30 minutes, then the cells were washed, and incubation with $Yb^{3+}[Zn(II)MC_{pyzHA}]$ took place for 15 minutes. For SN2 and cells2, incubation with $Yb^{3+}[Zn(II)MC_{pyzHA}]$ took place for 15 minutes, and then NAC was added and incubation with NAC took place for 30 minutes. The results in are shown in FIGS. 20C (corrected and normalized excitation) and 20D (corrected and normalized emission). The characteristic emission (FIG. 20, (B)), arising from Yb f-f transitions, show that luminescent properties of the $Yb^{3+}[Zn(II)MC_{pyzHA}]$ complexes did not change in cell supernatant or inside of the HeLa cells (with/without exposure to UV light). These results indicate that the cell structures remain intact.

Table 2, below, illustrates some of the photophysical parameters of $Yb^{3+}[Zn(II)MC_{pyzHA}]$ complexes in OPTI-MEM® media, cell supernatant (SN) and in HeLa cells (with/without exposure to UV light and with/without treatment with N-acetyl cysteine).

TABLE 2

| Condition | Quantum yield/% | $\tau_1/\mu s$ | $\tau_2/\mu s$ |
| --- | --- | --- | --- |
| OptiMEM | $1.25(1) \cdot 10^{-2}$ | 6.45(5): 89% | 24(1): 11% |
| OptiMEM-UV 1 h 30 min | $2.05(5) \cdot 10^{-2}$ | 7.03(3): 61% | 21.5(1): 39% |
| No UV: After 5 h of incubation with HeLa cells without illumination | $1.52(3) \cdot 10^{-2}$ | 6.47(4): 75% | 21.6(8): 25% |
| UV: After 5 h of incubation with HeLa cells with UV | $1.64(5) \cdot 10^{-2}$ | 6.51(8): 65% | 21(1): 35% |
| illumination (during 8 min) | | | |
| In HeLa cells | $2.14(6) \cdot 10^{-2}$ | | 23.6(7): 100% |
| No UV NAC (SN1*) | $1.08(1) \cdot 10^{-2}$ | 7.27(2): 91% | 50(2): 9% |
| No UV NAC (in cells1*) | n.a. | 7.5(4): 6% | 22.9(1): 94% |
| No UV NAC (SN2*) | $1.00(4) \cdot 10^{-2}$ | 6.72(3): 88% | 28.4(1): 12% |
| No UV NAC (in cells2*) | n.a. | 7.3(1): 7% | 23.6(2): 93% |
| UV NAC (SN2*) | $1.06(5) \cdot 10^{-2}$ | 6.80(9): 75% | 23(1): 25% |
| UV NAC (in cells2*) | n.a. | 8.7(5): 9% | 23.2(1): 91% |

$Yb^{3+}[Zn(II)MC_{pyzHA}]$ exhibit promising photophysical properties, which are among the highest values for quantum yields and luminescence lifetimes. The data in Table 2 are additional quantitative data showing that the MC stays intact in cell culture media and in the cells under different experimental conditions.

In cell culture media, the start of two lifetimes was observed, where the first lifetime is comparable with the one obtained for $Yb^{3+}[Zn(II)MC_{pyzHA}]$ in $H_2O$ while second lifetime was much longer. With the OPTI-MEM® media with $Yb^{3+}[Zn(II)MC_{pyzHA}]$ exposed to UV light, a higher percentage of 2. lifetime (39%) was seen, while without exposure to UV, 2. lifetime was 11%.

From these results, it is very important to highlight that "in cells" was dominating longer component under all experimental conditions.

More experiments need to be performed in order to explain the fact that inside of HeLa cells, the $Yb^{3+}[Zn(II)MC_{pyzHA}]$ had a dominating long lifetime, more than 90% for all experimental conditions.

Photophysical Properties of $Nd^{3+}[Zn(II)MC_{pyzHA}]$ in the HeLa Cancer Cells The $Nd^{3+}[Zn(II)MC_{pyzHA}]$ complexes were incorporated into OPTI-MEM® medium (without cells), and were incorporated in HeLa cells, both with and without exposure to UV light. The results are shown in FIG. 20, (E) (corrected and normalized excitation) and FIG. 20, (F) (corrected and normalized emission). The characteristic emission (FIG. 21, B), arising from Nd, show that luminescent properties of the $Nd^{3+}[Zn(II)MC_{pyzHA}]$ complexes did not change in OPTI-MEM® media or inside of the HeLa cells (with/without exposure to UV light). These results indicate that the cell structures remain intact.

Table 3, below, illustrates some of the photophysical parameters of $Nd^{3+}[Zn(II)MC_{pyzHA}]$ complexes in OPTI-MEM® media and in HeLa cells (with/without exposure to UV light).

TABLE 3

| Compound | Condition | Quantum yield/% | $\tau_1/\mu s$ | $\tau_2/\mu s$ |
| --- | --- | --- | --- | --- |
| $Nd^{III}$ MC | OptiMEM | $7.33(1) \cdot 10^{-3}$ | 0.256(6): 90% | 1.1(1): 10% |
| | OptiMEM-UV 1 h 30 min | $7.7(1) \cdot 10^{-3}$ | 0.352(2): 67% | 0.874(7): 33% |
| | No UV: After 5 h incubation with HeLa cells without illumination | $7.50(5) \cdot 10^{-3}$ | 0.261(1): 85% | 0.98(1): 15% |
| | UV: After 5 h incubation with HeLa cells with UV illumination (during 8 min) | $6.2(1) \cdot 10^{-3}$ | 0.376(3): 60% | 0.83(2): 40% |
| | In HeLa cells | | | 0.808(8): 100% |

The photophysical results for $Nd^{3+}[Zn(II)MC_{pyzHA}]$ in OPTI-MEM® media and in HeLa cells were similar to those for $Yb^{3+}[Zn(II)MC_{pyzHA}]$. In OPTI-MEM® media, there started to be a longer component. When exposing that medium to UV light, there was a higher contribution of the longer component. For $Nd^{3+}[Zn(II)MC_{pyzHA}]$ inside of HeLa cells, there was 100% of the longer component.

Example 8—Raman Spectroscopy

Raman spectroscopy maps were collected for living HeLa cells, HeLa cells that were fixed with paraformaldehyde (PFA), HeLa cells that were fixed with methanol (MeOH), and HeLa cells that were stained and fixed with $Yb^{3+}[Zn(II)MC_{pyzHA}]$ using the example method disclosed herein (as described in Example 1).

Fixation of the Cells with PFA (Paraformaldehyde):

Cells were seeded in an 8-well Lab Tek Chamber coverglass, as previously described in Example 1. Cells were washed trice with OPTI-MEM® (room temperature) and incubated with 4% PFA solution in PBS (Phosphate Buffered Saline) for 30 minutes at room temperature. After incubation with PFA, cells were washed trice with OPTI-MEM® (room temperature) and new reduced medium was added on the cells (OPTI-MEM®+2% of SVF).

Fixation of Cells with Methanol:

Cells were seeded in an 8-well Lab Tek Chamber coverglass, as previously described in Example 1. Cells were washed trice with OPTI-MEM® (room temperature) and incubated with ice-cold 100% methanol at −20° C. for 10 minutes. Cells were washed trice with OPTI-MEM® (room temperature) and new reduced medium was added on the cells (OPTI-MEM®+2% of SVF).

Figure 21:
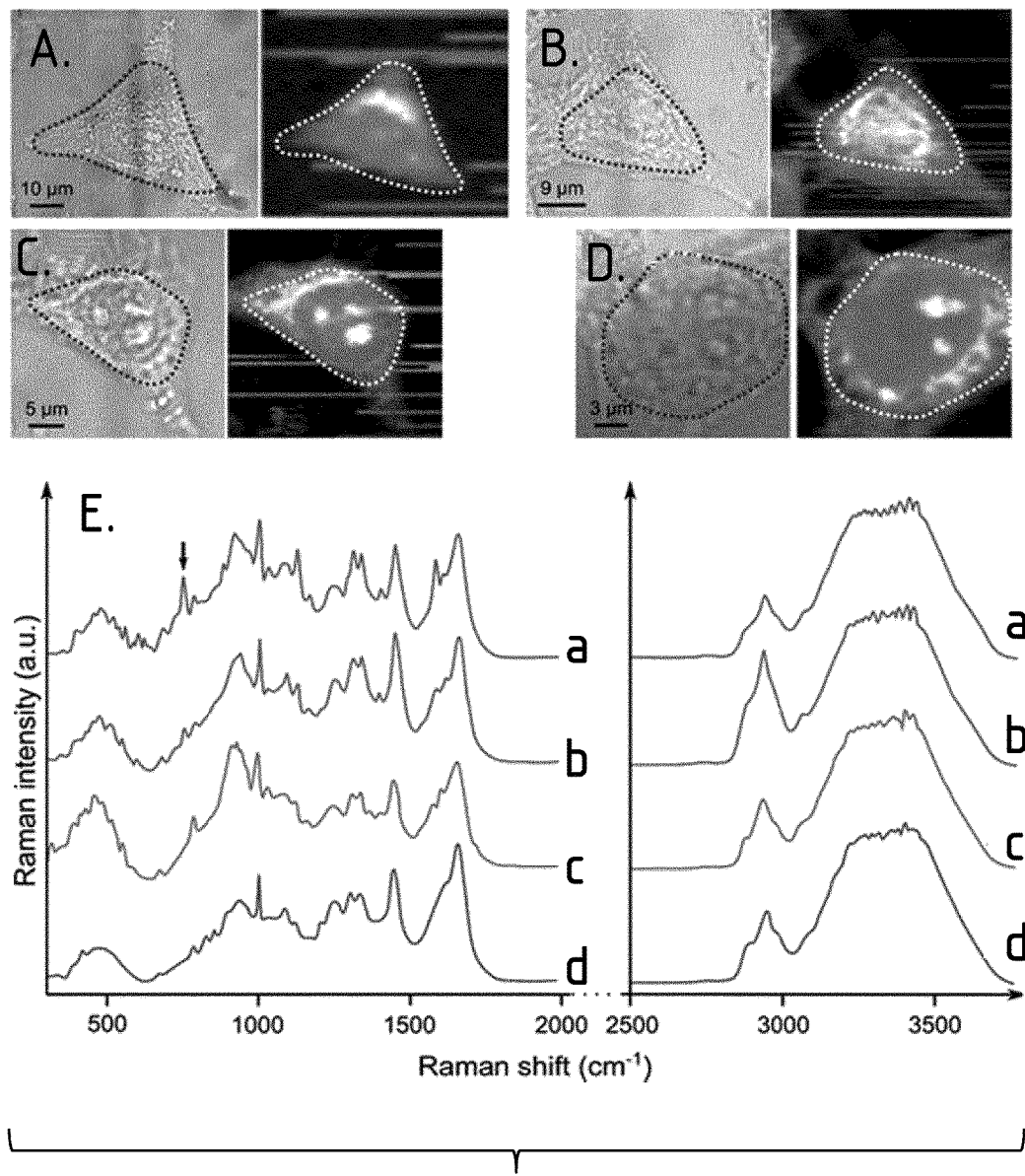
FIG. 21. (A) to (D) illustrate optical views and associated Raman spectroscopy mapping of CH bands intensities of (a) Live cell and cells fixed with (b) PFA, (c) Methanol and (d) Yb$^{3+}$[Zn(II)MC$_{pyzHA}$]. (E) shows the associated average spectra corresponding to the part of maximal CH Raman signal in a-d (areas surrounded by dashed lines in a-d). The decrease of the 751 cm$^{-1}$ peak intensity of cytochrome c for fixed cells in respect to live cells is observed (black arrow).

The areas corresponding to the cytoplasm and to the nucleus were selected manually on the different maps, FIG. 21, (A) to (D).

To study the changes between the different samples, a background subtraction was applied and the signal was collected in the range of 0-4000 $cm^{-1}$ in different cellular structures, cytoplasm and nucleus, allowing to observe the variations of specific vibrations arising from the nucleic acids and proteins, in particular, the CH vibrational bands at 2800-3300 $cm^{-1}$ that reflect a distribution of proteins, lipids and carbohydrates in cells and often used to localize cellular organelles, as well as OH band in the range of 3100-3650 $cm^{-1}$. The average spectrum corresponding to the one with the maximum CH bands signal (e.g. cytoplasm and nucleus) was extracted for each sample. Results indicate very similar biomolecular profiles of HeLa cells fixed with $Yb^{3+}[Zn(II)MC_{pyzHA}]$ to the ones fixed with PFA and methanol. Thus, the main difference in respect to the living cells was the decrease of the 752 $cm^{-1}$ peak intensity corresponding to the cytochrome c which has been already reported for the fixation with PFA (Okada et al. Proc Natl Acad Sci USA, 109 (2012) 28-32).

However, a more detailed analysis of Raman signal is required to fully quantify and identify corresponding peaks in order to completely understand changes in the biomolecular profile observed for the fixation with $Yb^{3+}[Zn(II)MC_{pyzHA}]$.

Photobleaching Experiments on Epifluorescence Microscope.

During the photobleaching experiments conducted under the epifluorescence microscope, necrotic HeLa cells labelled with PI were illuminated during 8 min with 550 nm band pass 25 nm filter and images were captured every 10 s with the following filter cube: 550 nm band pass 25 nm for the excitation and 605 nm band pass 70 nm for the emission. The same experiment was performed with $Yb^{3+}[Zn(II)MC_{pyzHA}]$ which was excited using a 447 nm band pass 60 nm filter and images were captured every 10 s with the following cube: 447 nm band pass 60 nm for the excitation and long pass 805 nm filter for $Yb^{3+}$ emission in the NIR range.

It is to be understood that the ranges provided herein include the stated range and any value or sub-range within the stated range. For example, a range from about 45 μM to about 400 μM should be interpreted to include not only the explicitly recited limits of about 90 μM to about 400 μM, but also to include individual values, such as 99.5 μM, 200 μM, etc., and sub-ranges, such as from about 100 μM to about 350 μM, etc. Furthermore, when "about" is utilized to describe a value, this is meant to encompass minor variations (up to +/−10%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

The invention claimed is:

1. A method for simultaneously fixing and staining cells, the method comprising:
   initially incubating the cells in a solution including a $Ln(III)Zn_{16}(HA\ ligand)_{16}$ metallacrown complex, wherein the HA ligand is a hydroximate ligand;
   exposing the incubating cells to ultraviolet (UV) light; and
   continuing to incubate the cells in the solution after UV light exposure.

2. The method of claim 1 wherein:
   the solution includes the $Ln(III)Zn_{16}(HA\ ligand)_{16}$ metallacrown complex in a medium; and
   a concentration of the $Ln(III)Zn_{16}(HA\ ligand)_{16}$ metallacrown complex in the solution ranges from about 90 μM to about 400 μM.

3. The method of claim 1, further comprising culturing the cells prior to incubating the cells in the solution.

4. The method of claim 1, wherein:
   initially incubating the cells is accomplished for a time (T1) ranging from about 10 minutes to about 3 hours;
   exposing the incubating cells to UV light is accomplished for a time (T2) ranging from about 5 minutes to about 10 minutes; and
   continuing to incubate the cells is accomplished for a time (T3) ranging from about 1 hour to about 2 hours.

5. The method as defined in claim 4, further comprising exposing the incubating cells to additional UV light for a time (T4) ranging from about 1 minute to about 5 minutes.

6. The method of claim 1, wherein the HA ligand of the $Ln(III)Zn_{16}(HA\ ligand)_{16}$ metallacrown complex is selected from the group consisting of pyrazinehydroximate, quinoxalinehydroximate, quinaldinehydroximate, and combinations thereof.

7. The method as defined in claim 6 wherein:
the Ln(III)Zn$_{16}$(HA ligand)$_{16}$ metallacrown complex is one of:

[Ln(III)Zn$_{16}$(pyrazinehydroximate)$_{16}$(pyridine)$_8$] counter ion;

[Ln(III)Zn$_{16}$(quinoxalinehydroximate)$_{16}$(pyridine)$_8$] counter ion; or

[Ln(III)Zn$_{16}$(quinaldinehydroximate)$_{16}$(pyridine)$_8$] counter ion;

wherein the Ln(M) is selected from the group consisting of Y$^{3+}$, La$^{3+}$, Ce$^{3+}$, Pr$^{3+}$, Nd$^{3+}$, Pm$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, Yb$^{3+}$, and Lu$^{3+}$; and wherein the counter ion is selected from the group consisting of a triflate, a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a phosphate, and a sulfonate.

8. The method as defined in claim 6 wherein:
the Ln(III)Zn$_{16}$(HA ligand)$_{16}$ metallacrown complex includes a mixture of metallacrown complexes;
each species in the metallacrown mixture is [Ln(III)Zn$_{16}$(pyrazinehydroximate)$_x$(quinoxalinehydroximate)$_y$(pyridine)$_8$] counter ion,
wherein x+y=16;
wherein the Ln(M) is selected from the group consisting of Y$^{3+}$, La$^{3+}$, Ce$^{3+}$, Pr$^{3+}$, Nd$^{3+}$, Pm$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, Yb$^{3+}$, and Lu$^{3+}$; and
wherein the counter ion is selected from the group consisting of a triflate, a mesylate, a besylate, a camsylate, an edisylate, an estolate, an esylate, a napsylate, a tosylate, a fluoride, a chloride, a bromide, an iodide, a nitrate, a sulfate, a carbonate, an acetate, a phosphate, and a sulfonate.

9. The method of claim 8, wherein x ranges from 8 to 13 and y ranges from 3 to 8.

10. The method of claim 1, wherein the medium is a serum-supplemented medium.

11. The method of claim 1, wherein the UV light is UV-A light.

12. The method of claim 1, wherein:
UV light exposure induces death of at least some of the cells; and
after continuing to incubate the cells, the Ln(III)Zn$_{16}$(HA ligand)$_{16}$ metallacrown complex is located in nuclei and cytoplasm of least some dead cells.

* * * * *